(12) United States Patent
Winkler et al.

(10) Patent No.: US 8,790,903 B2
(45) Date of Patent: *Jul. 29, 2014

(54) METABOLIC ENGINEERING OF XYLOSE-FERMENTING EUKARYOTIC CELLS

(75) Inventors: Aaron Adriaan Winkler, The Hague (NL); Sipko Maarten Kuyper, Delft (NL); Wilhelmus Theordorus Antonius Maria De Laat, Breda (NL); Johannes Pieter Van Dijken, Leidschendam (NL); Jacobus Thomas Pronk, Schipluiden (NL)

(73) Assignee: DSM IP Assets B.V., Heerlen (NL)

( * ) Notice: Subject to any disclaimer, the term of this patent is extended or adjusted under 35 U.S.C. 154(b) by 343 days.

This patent is subject to a terminal disclaimer.

(21) Appl. No.: 13/225,215

(22) Filed: Sep. 2, 2011

(65) Prior Publication Data

US 2012/0225451 A1    Sep. 6, 2012

Related U.S. Application Data

(66) Continuation of application No. 11/632,644, Substitute for application No. PCT/NL2005/000516, filed on Jul. 15, 2005, now Pat. No. 8,034,591.

(60) Provisional application No. 60/588,381, filed on Jul. 16, 2004, provisional application No. 60/589,833, filed on Jul. 22, 2004.

(30) Foreign Application Priority Data

Jul. 16, 2004 (EP) .................................... 04077073

(51) Int. Cl.
- *C12P 7/06* (2006.01)
- *C12N 9/00* (2006.01)
- *C12N 1/00* (2006.01)
- *C12N 15/00* (2006.01)
- *C07H 21/04* (2006.01)

(52) U.S. Cl.
USPC ... 435/161; 435/183; 435/254.11; 435/320.1; 536/23.2

(58) Field of Classification Search
None
See application file for complete search history.

(56) References Cited

FOREIGN PATENT DOCUMENTS

| | | |
|---|---|---|
| WO | 02/38740 | 5/2002 |
| WO | 03/062430 | 7/2003 |
| WO | WO 03/062430 | * 7/2003 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession Q8A9M2. Jun. 1, 2003.*
International Search Report PCT/NL2005/000516.
Marko Kuyper et al., Minimal metabolic engineering of *Saccharomyces cerevisiae* for efficient anaerobic xylose fermentation: a proof of principle (Fems Yeast Research, XP-002312911), Mar. 2004, pp. 655-664, vol. 4, No. 6, published by Elsevier.
K. L. Traff et al., Deletion of the GRE3 Aldose Reductase Gene and its influence on Xylose Metabolism in Recombinant Strains of *Saccharomyces cereviase* Expressing the xyIA and XKS1 Genes, (Applied and Environmental Microbiology—XP-002312912), Dec. 2001, pp. 5668-5674, vol. 67, No. 12, published by American Society for Microbiology.
Marko Kuyper et al., High-level functional expression of a fungal xylose isomerase: the key to efficient ethanolic fermentation of xylose by *Saccharomyces cerevisiae*?, (Fems Yeast Research, XP002312913), Oct. 2003, pp. 69-78, vol. 4, No. 1, published by Elsevier.
Lonn A. et al., Xylose isomerase activity influences xylose fermentation with recombinant *Saccharomyces cerevisiae* strains expressing mutated xyIA from *Thermus thermophilus*, (Enzyme and Microbial Technology, XP 002312914), Apr. 2003, pp. 567-573, vol. 32, No. 5, published by Elsevier.
Bjorn Johansson et al., The non-oxidative pentose phosphate pathway controls the fermentation rate xylose but not of xylose in *Sccharomyces cerevisiae* TMB3001, (Fems Yeast Research, XP-002966585), 2002, vol. 2, pp. 277-282, published by Elsevier Science, Tokyo, NL.
Kaisa Karhumaa et al., Investigation of limiting metabolic steps in the utilization of xylose by recombinant *Saccharomyces cerevisiae* using metabolic engineering, Yeast, 2005, vol. 22, pp. 359-368, published online Wiley InterScience.

* cited by examiner

*Primary Examiner* — Christian Fronda
(74) *Attorney, Agent, or Firm* — Browdy and Neimark, PLLC

(57) ABSTRACT

The present invention relates to genetic modifications in eukaryotic host cells that have been transformed to express a xylose isomerase that confers on the host cell the ability to isomerize xylose to xylulose. These genetic modifications are aimed at improving the efficiency of xylose metabolism and include. e.g., reduction of nonspecific aldose reductase activity, increased xylulose kinase activity and increased flux of the pentose phosphate pathway. The modified host cells of the invention are suitable for the production of a wide variety of fermentation products, including ethanol, in fermentation processes in which a source of xylose or a source of xylose and glucose are used as carbon source.

25 Claims, 5 Drawing Sheets

METABOLIC ENGINEERING OF XYLOSE-FERMENTING EUKARYOTIC CELLS

FIELD OF THE INVENTION

The present invention relates to further genetic modifications in eukaryotic host cells that have been transformed to express a xylose isomerase that confers the host cell the ability of isomerizing xylose to xylulose. The further genetic modifications are aimed at improving the efficiency of xylose metabolism and include e.g., reduction of nonspecific aldose reductase activity, increased xylulose kinase activity and increased flux of the pentose phosphate pathway. The modified host cells of the invention are suitable for the production of a wide variety of fermentation products in processes comprising xylose as carbon source.

BACKGROUND OF THE INVENTION

Economically viable ethanol production from the hemicellulose fraction of plant biomass requires the simultaneous conversion of both pentoses and hexoses at comparable rates and with high yields. Yeasts, in particular *Saccharomyces* spp., are the most appropriate candidates for this process since they can grow fast on hexoses, both aerobically and anaerobically. Furthermore they are much more resistant to the toxic environment of lignocellulose hydrolysates than (genetically modified) bacteria.

In previous studies evidence has been provided that metabolic engineering of *S. cerevisiae* for xylose utilization, should be based on the introduction of xylose isomerase (XI, EC 5.3.1.5) (Bruinenberg et al., 1983, *Eur J. Appl. Microbiol. Biotechnol.* 18:287-292). In contrast to strains that are based on xylose reductase (XR, EC 1.1.1.21) and xylitol dehydrogenase (XD, EC 1.1.1.9), strains expressing XI activity display high alcohol yields and hardly produce xylitol as has recently been demonstrated in WO 03/0624430 and Kuyper et al. 2004, *FEMS Yeast Res.* 4:655-664. From a theoretical point of view this is not surprising since the route via XR and XD leads to an obstruction in the NADH balance that in the absence of oxygen, can be relieved e.g., via xylitol formation.

WO03/0624430 discloses that the introduction of a functional *Piromyces* XI into *S. cerevisiae* allows slow metabolism of xylose via the endogenous xylulokinase (EC 2.7.1.17) encoded by XKS1 and the enzymes of the non-oxidative part of the pentose phosphate pathway and confers to the yeast transformants the ability to grow on xylose.

Kuyper et al. (supra) describe *S. cerevisiae* strains in which the *Piromyces* XI has been introduced and which are thereafter subjected to directed evolution in shake flasks show improved rates of xylose fermentation, but still required oxygen for growth. Further selection via a regime of extreme oxygen limitation under xylose excess, followed by anaerobic selection resulted in a laboratory strain (RWB202-AFX) which fulfils at least one of the prerequisites for hemicellulose utilization, namely an acceptable ethanol yield on xylose. However, the specific rate of ethanol production in this strain is still unacceptably low. In particular, the specific sugar consumption rate during growth on xylose (345 mg xylose/g biomass/h) is still ten-fold lower than on glucose. Attempts to further improve strain RWB202-AFX via evolutionary engineering have failed so far.

WO03/0624430 lists a number of alternative genetic modifications that may result in further improvement of the specific rates of ethanol production and/or sugar consumption on xylose in host cells expressing the *Piromyces* XI gene to a level that would be required for commercial hemicellulose utilization. These alternatives include: (a) increase transport of xylose into the host cell; (b) increased xylulose kinase activity; (c) increased flux of the pentose phosphate pathway; (d) decreased sensitivity to catabolite repression; (e) increased tolerance to ethanol, osmolarity or organic acids; and, (f) reduced production of by-products (such as e.g., xylitol, glycerol and/or acetic acid). More specifically, WO03/0624430 suggests to overexpress one or more of the genes encoding a hexose or pentose transporter, a xylulose kinase (such as the *S. cerevisiae* XKS1) an enzyme from the pentose phosphate pathway such as a transaldolase (TAL1) or a transketolase (TKL1) glycolytic enzymes, ethanologenic enzymes such as alcohol dehydrogenases, and/or to inactivate a hexose kinase gene, e.g., the *S. cerevisiae* HXK2 gene, the *S. cerevisiae* MIG1 or MIG2 genes, the (nonspecific) aldose reductase genes such as the *S. cerevisiae* GRE3 gene, or genes for enzymes involved in glycerol metabolism such as the *S. cerevisiae* glycerol-phosphate dehydrogenase 1 and/or 2 genes. WO03/0624430 however does not disclose which of these many alternatives actually does produce an improvement in the specific rates of ethanol production and/or xylose consumption in host cells carrying the *Piromyces* XI gene.

Karhumaa et al. (2004, "Development of a Xylose-growing *Saccharomyces cerevisiae* strain expressing bacterial xylose isomerase", Poster presentation at 2$^{nd}$ *Meeting on Physiology of Yeasts and Filamentous Fungi*; Mar. 24-28, 2004 Anglet, France, p 43; and, "New Xylose-growing *Saccharomyces cerevisiae* strain for biofuel ethanol production", Oral presentation at the 26*th Symposium on Biotechnology for Fuels and Chemicals*, May 9-12, 2004 Chattanooga Tenn., USA, p. 19) disclose a strain of *S. cerevisiae* expressing a bacterial XI from *Thermus thermophilus*. The strain further contains a number of the genetic modifications suggested in WO03/0624430: overexpression of xylulose kinase and all four enzymes of the non-oxidative pentose phosphate pathway as well as inactivation of the *S. cerevisiae* nonspecific aldose reductase gene (GRE3). However, despite these genetic modifications this strain is incapable of growth on xylose. Only after adaptation to aerobic growth on xylose a strain, TMB3050, was obtained that is capable of growth on xylose at a low rate ($\mu$=0.04 h$^{-1}$) and with a low specific xylose consumption rate of 4.3 mg xylose/g cells/h. Since undefined genetic modifications (accumulated during adaptation) are clearly required for growth on xylose in the first place, one cannot deduce from the work of Karhumaa et al. (supra) which, if any, of the defined genetic modifications (such as overexpression of xylulose kinase or any of the pentose phosphate pathway enzymes or inactivation of the aldose reductase gene) actually contribute to the ability of the adapted strain to grow on xylose.

It is therefore an object of the present invention to provide for eukaryotic host cells, such as fungal host cells, that are transformed with a XI gene that confers the ability to grow on xylose and which host cells have specific rates of xylose consumption and/or product (ethanol) formation that are compatible with commercial application of the host cells.

DESCRIPTION OF THE INVENTION

Definitions

Xylose Isomerase

The enzyme "xylose isomerase" (EC 5.3.1.5) is herein defined as an enzyme that catalyses the direct isomerization of D-xylose into D-xylulose and vice versa. The enzyme is also known as a D-xylose ketoisomerase. Some xylose isomerases are also capable of catalyzing the conversion between D-glucose and D-fructose and are therefore sometimes referred to as glucose isomerase. Xylose isomerases require bivalent cations like magnesium or manganese as cofactor. Xylose isomerases of the invention may be further defined by their amino acid sequence as herein described below. Likewise xylose isomerases may be defined by the nucleotide sequences encoding the enzyme as well as by nucleotide sequences hybridizing to a reference nucleotide sequence encoding a xylose isomerase as herein described below.

A unit (U) of xylose isomerase activity is herein defined as the amount of enzyme producing 1 nmol of xylulose per minute, under conditions as described by Kuyper et al. (2003, *FEMS Yeast Res.* 4: 69-78).

Xylulose Kinase

The enzyme "xylulose kinase" (EC 2.7.1.17) is herein defined as an enzyme that catalyses the reaction ATP+D-xylulose→ADP+D-xylulose 5-phosphate. The enzyme is also known as a phosphorylating xylulokinase, D-xyluloki-nase or ATP:D-xylulose 5-phosphotransferase. A xylulose kinase of the invention may be further defined by its amino acid sequence as herein described below. Likewise a xylulose kinase may be defined by the nucleotide sequences encoding the enzyme as well as by nucleotide sequences hybridizing to a reference nucleotide sequence encoding a xylulose kinase as herein described below. A unit of xylulokinase activity is defined in Example 1.13 herein.

Ribulose 5-phosphate Epimerase

The enzyme "ribulose 5-phosphate epimerase" (5.1.3.1) is herein defined as an enzyme that catalyses the epimerization of D-xylulose 5-phosphate into D-ribulose 5-phosphate and vice versa. The enzyme is also known as phosphoribulose epimerase; erythrose-4-phosphate isomerase; phosphoketo-pentose 3-epimerase; xylulose phosphate 3-epimerase; phos-phoketopentose epimerase; ribulose 5-phosphate 3-epime-rase; D-ribulose phosphate-3-epimerase; D-ribulose 5-phosphate epimerase; D-ribulose-5-P 3-epimerase; D-xy-lulose-5-phosphate 3-epimerase; pentose-5-phosphate 3-epi-merase; or D-ribulose-5-phosphate 3-epimerase. A ribulose 5-phosphate epimerase of the invention may be further defined by its amino acid sequence as herein described below. Likewise a ribulose 5-phosphate epimerase may be defined by the nucleotide sequences encoding the enzyme as well as by nucleotide sequences hybridizing to a reference nucleotide sequence encoding a ribulose 5-phosphate epimerase as herein described below.

Ribulose 5-phosphate Isomerase

The enzyme "ribulose 5-phosphate isomerase" (EC 5.3.1.6) is herein defined as an enzyme that catalyses direct isomerization of D-ribose 5-phosphate into D-ribulose 5-phosphate and vice versa. The enzyme is also known as phosphopentosisomerase; phosphoriboisomerase; ribose phosphate isomerase; 5-phosphoribose isomerase; D-ribose 5-phosphate isomerase; D-ribose-5-phosphate ketol-isomerase; or D-ribose-5-phosphate aldose-ketose-isomerase. A ribulose 5-phosphate isomerase of the invention may be further defined by its amino acid sequence as herein described below. Likewise a ribulose 5-phosphate isomerase may be defined by the nucleotide sequences encoding the enzyme as well as by nucleotide sequences hybridizing to a reference nucleotide sequence encoding a ribulose 5-phosphate isomerase as herein described below.

Transketolase

The enzyme "transketolase" (EC 2.2.1.1) is herein defined as an enzyme that catalyses the reaction:

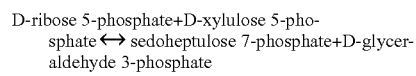

D-ribose 5-phosphate+D-xylulose 5-phosphate ↔ sedoheptulose 7-phosphate+D-glycer-aldehyde 3-phosphate and vice versa. The enzyme is also known as glycolaldehy-detransferase or sedoheptulose-7-phosphate:D-glyceralde-hyde-3-phosphate glycolaldehydetransferase. A transketo-lase of the invention may be further defined by its amino acid sequence as herein described below. Likewise a transketolase may be defined by the nucleotide sequences encoding the enzyme as well as by nucleotide sequences hybridizing to a reference nucleotide sequence encoding a transketolase as herein described below.

Transaldolase

The enzyme "transaldolase" (EC 2.2.1.2) is herein defined as an enzyme that catalyses the reaction:

sedoheptulose 7-phosphate+D-glyceraldehyde 3-phosphate ↔ D-erythrose 4-phosphate+D-fructose 6-phosphate and vice versa. The enzyme is also known as dihydroxyac-etone transferase; dihydroxyacetone synthase; formaldehyde transketolase; or sedoheptulose-7-phosphate:D-glyceralde-hyde-3-phosphate glyceronetransferase. A transaldolase of the invention may be further defined by its amino acid sequence as herein described below. Likewise a transaldolase may be defined by the nucleotide sequences encoding the enzyme as well as by nucleotide sequences hybridizing to a reference nucleotide sequence encoding a transaldolase as herein described below.

Aldose Reductase

The enzyme "aldose reductase" (EC 1.1.1.21) is herein defined as any enzyme that is capable of reducing xylose or xylulose to xylitol. In the context of the present invention an aldose reductase may be any nonspecific aldose reductase that is native (endogenous) to a host cell of the invention and that is capable of reducing xylose or xylulose to xylitol. Nonspecific aldose reductases catalyze the reaction:

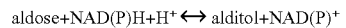

aldose+NAD(P)H+H$^+$ ↔ alditol+NAD(P)$^+$

The enzyme has a wide specificity and is also known as aldose reductase; polyol dehydrogenase (NADP$^+$); alditol: NADP oxidoreductase; alditol:NADP$^+$ 1-oxidoreductase; NADPH-aldopentose reductase; or NADPH-aldose reductase. A particular example of such an nonspecific aldose reductase that is endogenous to *S. cerevisiae* and that is encoded by the GRE3 gene (Träff et al., 2001, *Appl. Environ. Microbiol.* 67:5668-74). Thus, an aldose reductase of the invention may be further defined by its amino acid sequence as herein described below. Likewise an aldose reductase may be defined by the nucleotide sequences encoding the enzyme as well as by nucleotide sequences hybridizing to a reference nucleotide sequence encoding a aldose reductase as herein described below.

Sequence Identity and Similarity

Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (*Computational Molecular*

Biology, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heine, G., Academic Press, 1987; and *Sequence Analysis Primer*, Gribskov, M. and Devereux, J., eds., Stockton Press, New York, 1991; and Carillo, H., and Lipman, D., *SIAM J. Applied Math.*, 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g., the GCG program package (Devereux, J., et al., *Nucleic Acids Research* 12:387 (1984)), BestFit, BLASTP, BLASTN, and FASTA (Altschul, S. F. et al., *J. Mol. Biol.* 215:403-410 (1990). The BLAST X program is publicly available from NCBI and other sources (*BLAST Manual*, Altschul, S., et al., NCBI NLM NIH Bethesda, Md.; Altschul, S., et al., supra. The well-known Smith Waterman algorithm may also be used to determine identity.

Preferred parameters for polypeptide sequence comparison include the following: Algorithm: Needleman and Wunsch, *J. Mol. Biol.* 48:443-453 (1970); Comparison matrix: BLOSSUM62 from Hentikoff and Hentikoff, *Proc. Natl. Acad. Sci. USA.* 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch (supra); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Hybridizing Nucleic Acid Sequences

Nucleotide sequences encoding the enzymes of the invention may also be defined by their capability to hybridize with the nucleotide sequences of SEQ ID NO.'s 9-16 and 18, respectively, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridize at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e., at least for 10 hours and preferably washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridize at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e., at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

Operably Linked

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

Promoter

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most environmental and developmental conditions. An "inducible" promoter is a promoter that is active under environmental or developmental regulation.

Homologous

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically be operably linked to another promoter sequence or, if applicable, another secretory signal sequence and/or terminator sequence than in its natural environment. When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later. Preferably the region of identity is greater than about 5 bp, more preferably the region of identity is greater than 10 bp.

Heterologous

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e., combinations where at least two of the combined sequences are foreign with respect to each other.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

DETAILED DESCRIPTION OF THE INVENTION

The present invention relates to transformed eukaryotic host cells that have the ability of isomerizing xylose to xylulose as e.g., described in WO 03/0624430. The ability of isomerizing xylose to xylulose is conferred to the host cell by transformation of the host cell with a nucleic acid construct comprising a nucleotide sequence encoding a xylose isomerase. The transformed host cell's ability to isomerize xylose into xylulose is the direct isomerization of xylose to xylulose. This is understood to mean that xylose isomerized into xylulose in a single reaction catalyzed by a xylose isomerase, as opposed to the two step conversion of xylose into xylulose via a xylitol intermediate as catalyzed by xylose reductase and xylitol dehydrogenase, respectively.

The nucleotide sequence encodes a xylose isomerase that is preferably expressed in active form in the transformed host cell. Thus, expression of the nucleotide sequence in the host cell produces a xylose isomerase with a specific activity of at least 10 U xylose isomerase activity per mg protein at 30° C., preferably at least 20, 25, 30, 50, 100, 200, 300 or 500 U per mg at 30° C. The specific activity of the xylose isomerase expressed in the transformed host cell is herein defined as the amount of xylose isomerase activity units per mg protein of cell free lysate of the host cell, e.g., a yeast cell free lysate. Determination of the xylose isomerase activity, amount of protein and preparation of the cell free lysate are as described in Example 1.13. Accordingly, expression of the nucleotide sequence encoding the xylose isomerase in the host cell produces a xylose isomerase with a specific activity of at least 50 U xylose isomerase activity per mg protein at 30° C., preferably at least 100, 200, 500, 750 or 1000 U per mg at 30° C.

Preferably, expression of the nucleotide sequence encoding the xylose isomerase in the host cell produces a xylose isomerase with a $K_m$ for xylose that is less than 50, 40, 30 or 25 mM, more preferably, the $K_m$ for xylose is about 20 mM or less.

A preferred nucleotide sequence encoding the xylose isomerase may be selected from the group consisting of:
 (a) nucleotide sequences encoding a polypeptide comprising an amino acid sequence that has at least 60, 65, 70, 75, 80, 85, 90, 95, 97, 98, or 99% sequence identity with the amino acid sequence of SEQ ID NO. 1 and/or SEQ ID NO. 2;
 (b) nucleotide sequences comprising a nucleotide sequence that has at least 40, 50, 60, 70, 80, 90, 95, 97, 98, or 99% sequence identity with the nucleotide sequence of SEQ ID NO. 9 and/or SEQ ID NO. 10;
 (c) nucleotide sequences the complementary strand of which hybridizes to a nucleic acid molecule sequence of (a) or (b);
 (d) nucleotide sequences the sequence of which differs from the sequence of a nucleic acid molecule of (c) due to the degeneracy of the genetic code.

The nucleotide sequence encoding the xylose isomerase may encode either a prokaryotic or an eukaryotic xylose isomerase, i.e., a xylose isomerase with an amino acid sequence that is identical to that of a xylose isomerase that naturally occurs in the prokaryotic or eukaryotic organism. The present inventors have found that the ability of a particular xylose isomerase to confer to a eukaryotic host cell the ability to isomerize xylose into xylulose does not depend so much on whether the isomerase is of prokaryotic or eukaryotic origin. Rather this depends on the relatedness of the isomerase's amino acid sequence to that of the *Piromyces* sequence (SEQ ID NO. 1). Surprisingly, the eukaryotic *Piromyces* isomerase is more related to prokaryotic isomerases than to other known eukaryotic isomerases. The *Piromyces* isomerase shares 61% amino acid identity with a *Xanthomonas* enzyme and 82% with a *Bacteroides* enzyme (SEQ ID NO. 2), whereas it only shares 49-52% identity with several plant xylose isomerases. No reports have issued of a plant xylose isomerase that is actively expressed in yeast. In contrast, in Example 3 herein we describe that a *Bacteroides* xylose isomerase confers to a eukaryotic host cell the ability to isomerase xylose into xylulose and to grow on xylose as sole carbon source. Therefore, a preferred nucleotide sequence encodes a xylose isomerase having an amino acid sequence that is related to the *Piromyces* sequence as defined above. A preferred nucleotide sequence encodes a fungal xylose isomerase (e.g., from a *Basidiomycete*), more preferably a xylose isomerase from an anaerobic fungus, e.g., a xylose isomerase from an anaerobic fungus that belongs to the families *Neocallimastix, Caecomyces, Piromyces, Orpinomyces*, or *Ruminomyces*. Alternatively, a preferred nucleotide sequence encodes a bacterial xylose isomerase, preferably a Gram-negative bacterium, more preferably an isomerase from the class *Bacteroides*, or from the genus *Bacteroides*, most preferably from *B. thetaiotaomicron* (SEQ ID NO. 2).

To increase the likelihood that the xylose isomerase is expressed in active form in a eukaryotic host cell such as yeast, the nucleotide sequence encoding the xylose isomerase may be adapted to optimize its codon usage to that of the eukaryotic host cell. The adaptiveness of a nucleotide sequence encoding the xylose isomerase (or other enzymes of the invention, see below) to the codon usage of the host cell may be expressed as codon adaptation index (CAI). The codon adaptation index is herein defined as a measurement of the relative adaptiveness of the codon usage of a gene towards the codon usage of highly expressed genes. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, *Nucleic Acids Research* 15: 1281-1295; also see: Jansen et al., 2003, *Nucleic Acids Res.* 31:2242-51). An adapted nucleotide sequence preferably has a CAI of at least 0.2, 0.3, 0.4, 0.5, 0.6 or 0.7.

A host cell for transformation with the nucleotide sequence encoding the xylose isomerase as described above, preferably is a host capable of active or passive xylose transport into the cell. The host cell preferably contains active glycolysis. The host cell may further contain an endogenous pentose phosphate pathway and may contain endogenous xylulose kinase activity so that xylulose isomerized from xylose may be metabolized to pyruvate. The host further preferably contains enzymes for conversion of pyruvate to a desired fermentation product such as ethanol, lactic acid, 3-hydroxy-propionic acid, acrylic acid, acetic acid, succinic acid, citric acid, amino acids, 1,3-propane-diol, ethylene, glycerol, β-lactam antibiotics and cephalosporins.

A preferred host cell is a host cell that is naturally capable of alcoholic fermentation, preferably, anaerobic alcoholic fermentation. The host cell further preferably has a high tolerance to ethanol, a high tolerance to low pH (i.e., capable of growth at a pH lower than 5, 4, 3, or 2,5) and towards organic acids like lactic acid, acetic acid or formic acid and sugar degradation products such as furfural and hydroxy-methylfurfural, and a high tolerance to elevated temperatures. Any of these characteristics or activities of the host cell may be naturally present in the host cell or may be introduced or modified by genetic modification. A suitable host cell is a eukaryotic microorganism like e.g., a fungus, however, most suitable as host cell are yeasts or filamentous fungi.

Yeasts are herein defined as eukaryotic microorganisms and include all species of the subdivision Eumycotina (Alexopoulos, C. J., 1962, In: *Introductory Mycology*, John Wiley & Sons, Inc., New York) that predominantly grow in unicellular form. Yeasts may either grow by budding of a unicellular thallus or may grow by fission of the organism. Preferred yeasts as host cells belong to the genera *Saccharomyces, Kluyveromyces, Candida, Pichia, Schizosaccharomyces, Hansenula, Kloeckera, Schwanniomyces*, and *Yarrowia*. Preferably the yeast is capable of anaerobic fermentation, more preferably anaerobic alcoholic fermentation.

Filamentous fungi are herein defined as eukaryotic microorganisms that include all filamentous forms of the subdivision Eumycotina. These fungi are characterized by a vegetative mycelium composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism of most filamentous fungi is obligately aerobic. Preferred filamentous fungi as host cells belong to the genera *Aspergillus, Trichoderma, Humicola, Acremonium, Fusarium*, and *Penicillium*.

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Preferred yeast species as host cells include *S. cerevisiae, S. bulderi, S. barnetti, S. exiguus, S. uvarum, S. diastaticus, K. lactis, K. marxianus, K. fragilis*.

The host cell of the invention is thus a host cell that is transformed with a nucleic acid construct comprising the nucleotide sequence encoding the xylose isomerase as defined above. The nucleic acid construct comprising the xylose isomerase coding sequence preferably is capable of expression of the xylose isomerase in the host cell. To this end the nucleic acid construct may be constructed as described in e.g., WO 03/0624430. The host cell may comprise a single but preferably comprises multiple copies of the nucleic acid construct. The nucleic acid construct may be maintained episomally and thus comprise a sequence for autonomous replication, such as an ARS sequence. Suitable episomal nucleic acid constructs may e.g., be based on the yeast 2μ or pKD1 (Fleer et al., 1991, Biotechnology 9:968-975) plasmids. Preferably, however, the nucleic acid construct is integrated in one or more copies into the genome of the host cell. Integration into the host cell's genome may occur at random by illegitimate recombination but preferably nucleic acid construct is integrated into the host cell's genome by homologous recombination as is well known in the art of fungal molecular genetics (see e.g., WO 90/14423, EP-A-0 481 008, EP-A-0 635 574 and U.S. Pat. No. 6,265,186).

In a first aspect of the invention, the host cell of the invention comprises a genetic modification that increases the flux of the pentose phosphate pathway. In particular, the genetic modification causes an increased flux of the non-oxidative part pentose phosphate pathway. A genetic modification that causes an increased flux of the non-oxidative part of the pentose phosphate pathway is herein understood to mean a modification that increases the flux by at least a factor 1.1, 1.2, 1.5, 2, 5, 10 or 20 as compared to the flux in a strain which is genetically identical except for the genetic modification causing the increased flux. The flux of the non-oxidative part of the pentose phosphate pathway may be measured by growing the modified host on xylose as sole carbon source, determining the specific xylose consumption rate and subtracting the specific xylitol production rate from the specific xylose consumption rate, if any xylitol is produced. However, the flux of the non-oxidative part of the pentose phosphate pathway is proportional with the growth rate on xylose as sole carbon source, preferably with the anaerobic growth rate on xylose as sole carbon source. There is a linear relation between the growth rate on xylose as sole carbon source ($\mu_{max}$) and the flux of the non-oxidative part of the pentose phosphate pathway. The specific xylose consumption rate ($Q_s$) is equal to the growth rate ($\mu$) divided by the yield of biomass on sugar ($Y_{xs}$) because the yield of biomass on sugar is constant (under a given set of conditions: anaerobic, growth medium, pH, genetic background of the strain, etc.; i.e., $Q_s = \mu/Y_{xs}$). Therefore the increased flux of the non-oxidative part of the pentose phosphate pathway may be deduced from the increase in maximum growth rate under these conditions.

Genetic modifications that increase the flux of the pentose phosphate pathway may be introduced in the host cell in various ways. These including e.g., achieving higher steady state activity levels of xylulose kinase and/or one or more of the enzymes of the non-oxidative part pentose phosphate pathway and/or a reduced steady state level of nonspecific aldose reductase activity. These changes in steady state activity levels may be effected by selection of mutants (spontaneous or induced by chemicals or radiation) and/or by recombinant DNA technology e.g., by overexpression or inactivation, respectively, of genes encoding the enzymes or factors regulating these genes.

In a preferred host cell, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate epimerase, transketolase and transaldolase. Various combinations of enzymes of the (non-oxidative part) pentose phosphate pathway may be overexpressed. E.g., the enzymes that are overexpressed may be at least the enzymes ribulose-5-phosphate isomerase and ribulose-5-phosphate epimerase; or at least the enzymes ribulose-5-phosphate isomerase and transketolase; or at least the enzymes ribulose-5-phosphate isomerase and transaldolase; or at least the enzymes ribulose-5-phosphate epimerase and transketolase; or at least the enzymes ribulose-5-phosphate epimerase and transaldolase; or at least the enzymes transketolase and transaldolase; or at least the enzymes ribulose-5-phosphate epimerase, transketolase and transaldolase; or at least the enzymes ribulose-5-phosphate isomerase, transketolase and transaldolase; or at least the enzymes ribulose-5-phosphate isomerase, ribulose-5-phosphate epimerase, and transaldolase; or at least the enzymes ribulose-5-phosphate isomerase, ribulose-5-phosphate epimerase, and transketolase. In one embodiment of the invention each of the enzymes ribulose-5-phosphate isomerase, ribulose-5-phosphate epimerase, transketolase and transaldolase are overexpressed in the host cell. More preferred is a host cell in which the genetic modification comprises at least overexpression of both the enzymes transketolase and transaldolase as such a host cell is already capable of anaerobic growth on xylose. In fact, under some conditions we have found that host cells overexpressing only the transketolase and the transaldolase already have the same anaerobic growth rate on xylose as do host cells that overexpress all four of the enzymes, i.e., the ribulose-5-phosphate isomerase, ribulose-5-phosphate epimerase, transketolase and transaldolase. Moreover, host cells overexpressing both of the enzymes ribulose-5-phosphate isomerase and ribulose-5-phosphate epimerase are preferred over host cells overexpressing only the isomerase or only the epimerase as overexpression of only one of these enzymes may produce metabolic imbalances.

There are various means available in the art for overexpression of enzymes in the host cells of the invention. In particular, an enzyme may be overexpressed by increasing the copy number of the gene coding for the enzyme in the host cell, e.g., by integrating additional copies of the gene in the host cell's genome, by expressing the gene from an episomal multicopy expression vector or by introducing a episomal expression vector that comprises multiple copies of the gene.

Alternatively overexpression of enzymes in the host cells of the invention may be achieved by using a promoter that is not native to the sequence coding for the enzyme to be overexpressed, i.e., a promoter that is heterologous to the coding sequence to which it is operably linked. Although the promoter preferably is heterologous to the coding sequence to which it is operably linked, it is also preferred that the promoter is homologous, i.e., endogenous to the host cell. Preferably the heterologous promoter is capable of producing a higher steady state level of the transcript comprising the coding sequence (or is capable of producing more transcript molecules, i.e., mRNA molecules, per unit of time) than is the promoter that is native to the coding sequence, preferably under conditions where xylose or xylose and glucose are available as carbon sources, more preferably as major carbon sources (i.e., more than 50% of the available carbon source consists of xylose or xylose and glucose), most preferably as sole carbon sources. Suitable promoters in this context include both constitutive and inducible natural promoters as well as engineered promoters. A preferred promoter for use in the present invention will in addition be insensitive to catabolite (glucose) repression and/or will preferably not require xylose for induction.

Promoters having these characteristics are widely available and known to the skilled person. Suitable examples of such promoters include e.g., promoters from glycolytic genes, such as the phosphofructokinase (PPK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADH1, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics.

The coding sequence used for overexpression of the enzymes preferably is homologous to the host cell of the invention. However, coding sequences that are heterologous to the host cell of the invention may likewise be applied.

A nucleotide sequence used for overexpression of ribulose-5-phosphate isomerase in the host cell of the invention is a nucleotide sequence encoding a polypeptide with ribulose-5-phosphate isomerase activity, whereby preferably the polypeptide has an amino acid sequence having at least 50, 60, 70, 80, 90 or 95% identity with SEQ ID NO. 4 or whereby the nucleotide sequence is capable of hybridizing with the nucleotide sequence of SEQ ID NO. 12, under moderate conditions, preferably under stringent conditions.

A nucleotide sequence used for overexpression of ribulose-5-phosphate epimerase in the host cell of the invention is a nucleotide sequence encoding a polypeptide with ribulose-5-phosphate epimerase activity, whereby preferably the polypeptide has an amino acid sequence having at least 50, 60, 70, 80, 90 or 95% identity with SEQ ID NO. 5 or whereby the nucleotide sequence is capable of hybridizing with the nucleotide sequence of SEQ ID NO. 13, under moderate conditions, preferably under stringent conditions.

A nucleotide sequence used for overexpression of transketolase in the host cell of the invention is a nucleotide sequence encoding a polypeptide with transketolase activity, whereby preferably the polypeptide has an amino acid sequence having at least 50, 60, 70, 80, 90 or 95% identity with SEQ ID NO. 6 or whereby the nucleotide sequence is capable of hybridizing with the nucleotide sequence of SEQ ID NO. 14, under moderate conditions, preferably under stringent conditions.

A nucleotide sequence used for overexpression of transaldolase in the host cell of the invention is a nucleotide sequence encoding a polypeptide with transaldolase activity, whereby preferably the polypeptide has an amino acid sequence having at least 50, 60, 70, 80, 90 or 95% identity with SEQ ID NO. 7 or whereby the nucleotide sequence is capable of hybridizing with the nucleotide sequence of SEQ ID NO. 15, under moderate conditions, preferably under stringent conditions.

Overexpression of an enzyme, when referring to the production of the enzyme in a genetically modified host cell, means that the enzyme is produced at a higher level of specific enzymatic activity as compared to the unmodified host cell under identical conditions. Usually this means that the enzymatically active protein (or proteins in case of multi-subunit enzymes) is produced in greater amounts, or rather at a higher steady state level as compared to the unmodified host cell under identical conditions. Similarly this usually means that the mRNA coding for the enzymatically active protein is produced in greater amounts, or again rather at a higher steady state level as compared to the unmodified host cell under identical conditions. Overexpression of an enzyme is thus preferably determined by measuring the level of the enzyme's specific activity in the host cell using appropriate enzyme assays as described herein. Alternatively, overexpression of the enzyme may determined indirectly by quantifying the specific steady state level of enzyme protein, e.g., using antibodies specific for the enzyme, or by quantifying the specific steady level of the mRNA coding for the enzyme. The latter may particularly be suitable for enzymes of the pentose phosphate pathway for which enzymatic assays are not easily feasible as substrates for the enzymes are not commercially available. Preferably in the host cells of the invention, an enzyme to be overexpressed is overexpressed by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

In a second aspect of the invention, the host cell of the invention comprises a genetic modification that increases the specific xylulose kinase activity. Preferably the genetic modification causes overexpression of a xylulose kinase, e.g., by overexpression of a nucleotide sequence encoding a xylulose kinase. The gene encoding the xylulose kinase may be endogenous to the host cell or may be a xylulose kinase that is heterologous to the host cell. A nucleotide sequence used for overexpression of xylulose kinase in the host cell of the invention is a nucleotide sequence encoding a polypeptide with xylulose kinase activity, whereby preferably the polypeptide has an amino acid sequence having at least 50, 60, 70, 80, 90 or 95% identity with SEQ ID NO. 3 or whereby the nucleotide sequence is capable of hybridizing with the nucleotide sequence of SEQ ID NO. 11, under moderate conditions, preferably under stringent conditions.

A particularly preferred xylulose kinase is a xylose kinase that is related to the xylulose kinase from Piromyces (xylB; see WO 03/0624430). This Piromyces xylulose kinase is actually more related to prokaryotic kinase than to all of the known eukaryotic kinases such as the yeast kinase (SEQ ID NO. 3). The eukaryotic xylulose kinases have been indicated as non-specific sugar kinases, which have a broad substrate range that includes xylulose. In contrast, the prokaryotic xylulose kinases, to which the Piromyces kinase is most closely related, have been indicated to be more specific kinases for xylulose, i.e., having a narrower substrate range. Therefore, a more preferred nucleotide sequence for use in overexpression of xylulose kinase in the host cell of the invention is a nucleotide sequence encoding a polypeptide with xylulose kinase activity, whereby preferably the polypeptide has an amino acid sequence having at least 45, 50, 55, 60, 65, 70, 80, 90 or 95% identity with SEQ ID NO. 17 or whereby the nucleotide sequence is capable of hybridizing with the nucleotide sequence of SEQ ID NO. 18, under moderate conditions, preferably under stringent conditions.

In the host cells of the invention, genetic modification that increases the specific xylulose kinase activity may be combined with any of the modifications increasing the flux of the pentose phosphate pathway as described above, but this combination is not essential for the invention. Thus, a host cell of the invention comprising only a genetic modification that increases the specific xylulose kinase activity is specifically included in the invention. The various means available in the art for achieving and analyzing overexpression of a xylulose kinase in the host cells of the invention are the same as described above for enzymes of the pentose phosphate pathway. Preferably in the host cells of the invention, a xylulose kinase to be overexpressed is overexpressed by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

In a third aspect of the invention, the host cell of the invention comprises a genetic modification that reduces non-specific aldose reductase activity in the host cell. Preferably, nonspecific aldose reductase activity is reduced in the host cell by one or more genetic modifications that reduce the expression of or inactivates a gene encoding an nonspecific aldose reductase. Preferably, the genetic modifications reduce or inactivate the expression of each endogenous copy of a gene encoding an nonspecific aldose reductase in the host cell. Host cells may comprise multiple copies of genes encoding nonspecific aldose reductases as a result of di-, poly- or aneuploidy, and/or the host cell may contain several different (iso)enzymes with aldose reductase activity that differ in amino acid sequence and that are each encoded by a different gene. Also in such instances preferably the expression of each gene that encodes an nonspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of nonspecific aldose reductase activity in the host cell. A nucleotide sequence encoding an aldose reductase whose activity is to be reduced in the host cell of the invention is a nucleotide sequence encoding a polypeptide with aldose reductase activity, whereby preferably the polypeptide has an amino acid sequence having at least 50, 60, 70, 80, 90 or 95% identity with SEQ ID NO. 8 or whereby the nucleotide sequence is capable of hybridizing with the nucleotide sequence of SEQ ID NO. 16 under moderate conditions, preferably under stringent conditions.

In the host cells of the invention, genetic modification that reduces nonspecific aldose reductase activity in the host cell may be combined with any of the modifications increasing the flux of the pentose phosphate pathway and/or with any of the modifications increasing the specific xylulose kinase activity in the host cells as described above, but these combinations are not essential for the invention. Thus, a host cell of the invention comprising only a genetic modification that reduces nonspecific aldose reductase activity in the host cell is specifically included in the invention.

In a further aspect the invention relates to modified host cells that are further adapted to xylose utilization by selection of mutants, either spontaneous or induced (e.g., by radiation or chemicals), for growth on xylose, preferably on xylose as sole carbon source, and more preferably under anaerobic conditions. Selection of mutants may be performed by serial passaging of cultures as e.g., described by Kuyper et al. (2004, FEMS Yeast Res. 4: 655-664) or by cultivation under selective pressure in a chemostat culture as is described in Example 4 herein.

In a preferred host cell of the invention at least one of the genetic modifications described above, including modifications obtained by selection of mutants, confer to the host cell the ability to grow on xylose as carbon source, preferably as sole carbon source, and preferably under anaerobic conditions. Preferably the modified host cell produce essentially no xylitol, e.g., the xylitol produced is below the detection limit or e.g., less than 5, 2, 1, 0.5, or 0.3% of the carbon consumed on a molar basis.

Preferably the modified host cell has the ability to grow on xylose as sole carbon source at a rate of at least 0.05, 0.1, 0.2, 0.25 or 0.3 $h^{-1}$ under aerobic conditions, or, if applicable, at a rate of at least 0.03, 0.05, 0.07, 0.08, 0.09, 0.1, 0.12, 0.15 or 0.2 $h^{-1}$ under anaerobic conditions. Preferably the modified host cell has the ability to grow on a mixture of glucose and xylose (in a 1:1 weight ratio) as sole carbon source at a rate of at least 0.05, 0.1, 0.2, 0.25 or 0.3 $h^{-1}$ under aerobic conditions, or, if applicable, at a rate of at least 0.03, 0.05, 0.1, 0.12, 0.15, or 0.2 $h^{-1}$ under anaerobic conditions.

Preferably, the modified host cell has a specific xylose consumption rate of at least 346, 350, 400, 500, 600, 750, or 1000 mg xylose/g cells/h. Preferably, the modified host cell has a yield of fermentation product (such as ethanol) on xylose that is at least 55, 60, 70, 80, 85, 90, 95 or 98% of the host cell's yield of fermentation product (such as ethanol) on glucose. More preferably, the modified host cell's yield of fermentation product (such as ethanol) on xylose is equal to the host cell's yield of fermentation product (such as ethanol) on glucose. Likewise, the modified host cell's biomass yield on xylose is preferably at least 55, 60, 70, 80, 85, 90, 95 or 98% of the host cell's biomass yield on glucose. More preferably, the modified host cell's biomass yield on xylose is equal to the host cell's biomass yield on glucose. It is understood that in the comparison of yields on glucose and xylose both yields are compared under aerobic conditions or both under anaerobic conditions.

In a preferred aspect, the modified host cell of the invention is a host cell for the production of ethanol. In another aspect the invention relates to a transformed host cell for the production of fermentation products other than ethanol. Such non-ethanolic fermentation products include in principle any bulk or fine chemical that is producible by a eukaryotic microorganism such as a yeast or a filamentous fungus. Such fermentation products include e.g., lactic acid, 3-hydroxy-propionic acid, acrylic acid, acetic acid, succinic acid, citric acid, amino acids, 1,3-propane-diol, ethylene, glycerol, β-lactam antibiotics and cephalosporins. A preferred modified host cell of the invention for production of non-ethanolic fermentation products is a host cell that contains a genetic modification that results in decreased alcohol dehydrogenase activity.

In a further aspect the invention relates to fermentation processes in which the modified host cells of the invention are used for the fermentation of a carbon source comprising a source of xylose, such as xylose. In addition to a source of xylose the carbon source in the fermentation medium may also comprise a source of glucose. The source of xylose or glucose may be xylose or glucose as such or may be any carbohydrate oligo- or polymer comprising xylose or glucose units, such as e.g., lignocellulose, xylans, cellulose, starch and the like. For release of xylose or glucose units from such carbohydrates, appropriate carbohydrases (such as xylanases, glucanases, amylases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g., by using rate-limiting amounts of the carbohydrases. This, in turn, will prevent repression of systems required for metabolism and transport of non-glucose sugars such as xylose. In a preferred process the modified host cell ferments both the xylose and glucose, preferably simultaneously in which case preferably a modified host cell is used which is insensitive to glucose repression to prevent diauxic growth. In addition to a source of xylose (and glucose) as carbon source, the fermentation medium will further comprise the appropriate ingredient required for growth of the modified host cell. Compositions of fermentation media for growth of microorganisms such as yeasts are well known in the art.

The fermentation process is a process for the production of a fermentation product such as e.g., ethanol, lactic acid, 3-hydroxy-propionic acid, acrylic acid, acetic acid, succinic acid, citric acid, amino acids, 1,3-propane-diol, ethylene, glycerol, β-lactam antibiotics, such as Penicillin G or Penicillin V and fermentative derivatives thereof, and cephalosporins. The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e., oxygen consumption is not detectable), and wherein organic molecules serve as both electron donor and electron acceptors. In the absence of oxygen, NADH produced in glycolysis and biomass formation, cannot be oxidized by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, amino acids, 1,3-propane-diol, ethylene, glycerol, β-lactam antibiotics and cephalosporins.

The fermentation process is preferably run at a temperature that is optimal for the modified host cell. Thus, for most yeasts or fungal host cells, the fermentation process is performed at a temperature which is less than 42° C., preferably less than 38° C. For yeast or filamentous fungal host cells, the fermentation process is preferably performed at a temperature which is lower than 35, 33, 30 or 28° C. and at a temperature which is higher than 20, 22, or 25° C.

A preferred process is a process for the production of ethanol, whereby the process comprises the steps of: (a) fermenting a medium containing a source of xylose with a modified host cell as defined above, whereby the host cell ferments xylose to ethanol; and optionally, (b) recovery of the ethanol. The fermentation medium may also comprise a source of glucose that is also fermented to ethanol. In the process the volumetric ethanol productivity is preferably at least 0.5, 1.0, 1.5, 2.0, 2.5, 3.0, 5.0 or 10.0 g ethanol per liter per hour. The ethanol yield on xylose and/or glucose in the process preferably is at least 50, 60, 70, 80, 90, 95 or 98%. The ethanol yield is herein defined as a percentage of the theoretical maximum yield, which, for glucose and xylose is 0.51 g. ethanol per g. glucose or xylose.

In a further aspect the invention relates to a process for producing a fermentation product selected from the group consisting of lactic acid, 3-hydroxy-propionic acid, acrylic acid, acetic acid, succinic acid, citric acid, amino acids, 1,3-propane-diol, ethylene, glycerol, β-lactam antibiotics and cephalosporins. The process preferably comprises the steps of (a) fermenting a medium containing a source of xylose with a modified host cell as defined herein above, whereby the host cell ferments xylose to the fermentation product, and optionally, (b) recovery of the fermentation product. In a preferred process, the medium also contains a source of glucose.

Genetic Modifications

For overexpression of enzymes in the host cells of the inventions as described above, as well as for additional genetic modification of host cells, preferably yeasts, host cells are transformed with the various nucleic acid constructs of the invention by methods well known in the art. Such methods are e.g., known from standard handbooks, such as Sambrook and Russell (2001) *Molecular Cloning: A Laboratory Manual* (3$^{rd}$ edition), Cold Spring Harbor Laboratory, Cold Spring Harbor Laboratory Press, or F. Ausubel et al., eds., *Current Protocols in Molecular Biology*, Green Publishing and Wiley Interscience, New York (1987). Methods for transformation and genetic modification of fungal host cells are known from e.g., EP-A-0 635 574, WO98/46772, WO99/60102 and WO00/37671.

Promoters for use in the nucleic acid constructs for overexpression of enzymes in the host cells of the invention have been described above. In the nucleic acid constructs for overexpression, the 3'-end of the nucleotide acid sequence encoding the enzyme(s) preferably is operably linked to a transcription terminator sequence. Preferably the terminator sequence is operable in a host cell of choice, such as e.g., the yeast species of choice. In any case the choice of the terminator is not critical; it may e.g., be from any yeast gene, although terminators may sometimes work if from a non-yeast, eukaryotic, gene. The transcription termination sequence further preferably comprises a polyadenylation signal.

Optionally, a selectable marker may be present in the nucleic acid construct. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g., dihydrofolate reductase, hygromycin-B-phosphotransferase, 3'-O-phosphotransferase II (kanamycin, neomycin and G418 resistance). Although the of antibiotic resistance markers may be most convenient for the transformation of polyploid host cells, preferably however, non-antibiotic resistance markers are used, such as auxotrophic markers (URA3, TRP1, LEU2) or the *S. pombe* TPI gene (described by Russell P R, 1985, Gene 40: 125-130). In a preferred embodiment the host cells transformed with the nucleic acid constructs are marker gene free. Methods for constructing recombinant marker gene free microbial host cells are disclosed in EP-A-0 635 574 and are based on the use of bidirectional markers such as the *A. nidulans* amdS (acetamidase) gene or the yeast URA3 and LYS2 genes. Alternatively, a screenable marker such as Green Fluorescent Protein, lacZ, luciferase, chloramphenicol acetyltransferase, beta-glucuronidase may be incorporated into the nucleic acid constructs of the invention allowing to screen for transformed cells.

Optional further elements that may be present in the nucleic acid constructs of the invention include, but are not limited to, one or more leader sequences, enhancers, integration factors, and/or reporter genes, intron sequences, centromeres, telomeres and/or matrix attachment (MAR) sequences. The nucleic acid constructs of the invention may further comprise a sequence for autonomous replication, such as an ARS sequence. Suitable episomal nucleic acid constructs may e.g., be based on the yeast 2μ or pKD1 (Fleer et al., 1991, Biotechnology 9:968-975) plasmids. Alternatively the nucleic acid construct may comprise sequences for integration, preferably by homologous recombination. Such sequences may thus be sequences homologous to the target site for integration in the host cell's genome. The nucleic acid constructs of the invention can be provided in a manner known per se, which generally involves techniques such as restricting and linking nucleic acids/nucleic acid sequences, for which reference is made to the standard handbooks, such as Sambrook and Russell (supra).

Methods for inactivation and gene disruption in yeast or filamentous fungi are well known in the art (see e.g., Fincham, 1989, *Microbiol Rev.* 53:148-70 and EP-A-0 635 574).

Figure 1A:
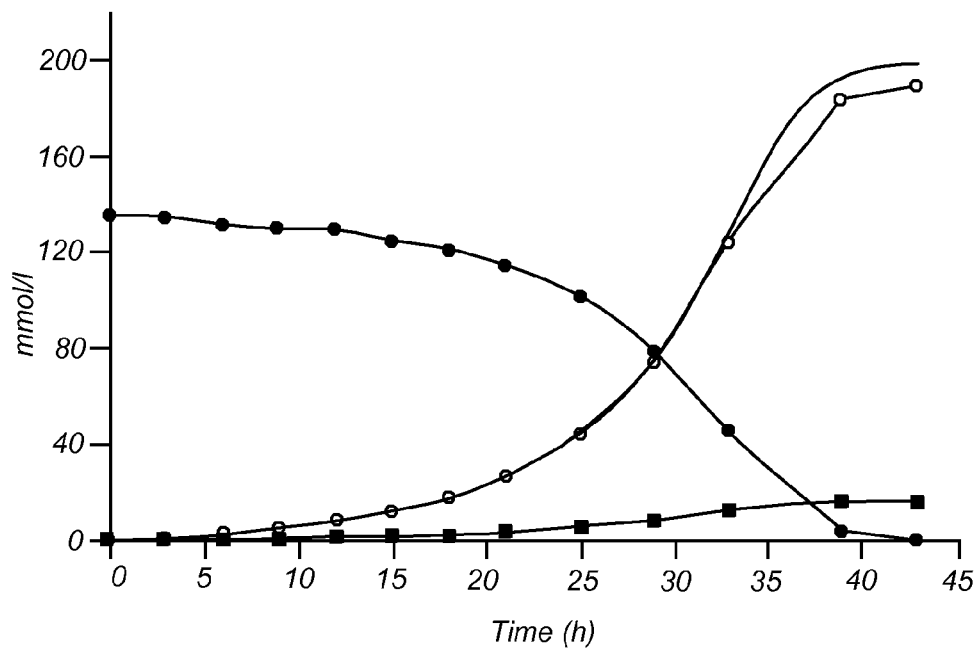
FIG. 1.

Typical graph of anaerobic growth of strain RWB 212 in fermentors on synthetic medium with 2% (w/v) xylose as the carbon source, duplicate experiments differed by less than 5%. Panel A: Xylose (●), ethanol (○), glycerol (■) and cumulative $CO_2$ produced per liter as deduced from gas analysis (-). Panel B: dry weight (●), acetate (○), xylitol (□), succinate (▲), lactate (Δ).

FIG. 2.

Typical graph of anaerobic growth of strain RWB 212 in fermenters on synthetic medium with 2% (w/v) glucose and 2% (w/v) xylose as the carbon source, duplicate experiments differed by less than 5%. Panel A: Glucose (●), xylose (○), ethanol (■), glycerol (□) and cumulative $CO_2$ produced per liter as deduced from gas analysis (-). Panel B: dry weight (●), acetate (○), xylitol (■), lactate (□) succinate (▲).

FIG. 3.

Panel A: Residual xylose concentrations during anaerobic chemostat cultivation of RWB 212 on 30 g/l xylose as the carbon source. Data presented are the average of two independent chemostats and the experimental deviations.

Panel B: Culture dry weight during anaerobic chemostat cultivation of RWB 212 on 30 g/l xylose as the carbon source. Data presented are the average of two independent chemostats and the experimental deviations.

FIG. 4.

Carbon dioxide production profiles of three xylose metabolizing strains in anaerobic batch cultivations on glucose and xylose (20 g/l each). Exact experimental conditions varied so actual numeric values may not be compared.

FIG. 5.

Concentrations of glucose, xylose, ethanol, glycerol and $CO_2$ measured during two independent anaerobic fermentor batches on 2% glucose and 2% xylose of selected strains originating from RWB 212.

EXAMPLES

1. Materials and Methods 1.1. Plasmid Construction

In order to integrate the TPI1 promoter in front of our target genes several plasmids were constructed. First the TPI1 promoter was cut as a XhoI-EcoRV fragment from pYX012-Aat (A. A. Winkler, derivative of pYX012 (R&D Systems, Minneapolis, Minn., USA)) and ligated to pUG6 [3] cut with SalI-PvuII. This gave us pUG6$P_{TPI}$, which could then be used to PCR a Kanlox-$P_{TPI}$ integration cassette.

In cases were putative ORF's were located very close to the ATG of the target genes, we cloned those genes into pUG6$P_{TPI}$. A 0.8 kb RPE1 fragment and a 2.3 kb TKL1 fragment were isolated from gel and cut with EcoRI and XhoI (present in the primers, see Table 3) and ligated into pUG6$P_{TPI}$ digested with EcoRI-SalI, resulting in pUG6$P_{TPI}$-RPE1 and pUG6$P_{TPI}$-TKL1.

In order to increase the activity of xylulokinase the XKS1 gene was amplified by PCR as a SpeI-SalI fragment (sites in the primers, see Table 3) and cloned into p415ADH [4] cut with XbaI-XhoI, resulting in p415ADHXKS.

Restriction endonucleases (New England Biolabs, Beverly, Mass., USA and Roche, Basel, Switzerland) and DNA ligase (Roche) were used according to the manufacturers' specifications. Plasmid isolation from *E. coli* was performed with the Qiaprep spin miniprep kit (Qiagen, Hilden, Germany). DNA fragments were separated on a 1% agarose (Sigma, St. Louis, Mo., USA) gel in 1×TBE [5]. Isolation of fragments from gel was carried out with the Qiaquick gel extraction kit (Quiagen). Amplification of RPE1, TKL1 and XKS1 was done with $Vent_R$ DNA polymerase (New England Biolabs) according to the manufacturer's specification. The template was chromosomal DNA of CEN.PK113-7D (wt). The polymerase chain reaction (PCR) was performed in a Biometra TGradient Thermocycler (Biometra, Göttingen, Germany) with the following settings: 30 cycles of 1 min annealing at 60° C., 3 min extension at 75° C. and 1 min denaturing at 94° C.

1.2. Strains and Media

The *Saccharomyces cerevisiae* strain used in this study is RWB212 (MATA ura3-52 leu2-112 loxP-$P_{TPI}$::(−266,−1) TAL1 gre3::hphMX pUGP$_{TPI}$-TKL1 pUGP$_{TPI}$-RPE1 KanloxP-$P_{TPI}$::(−?,−1)RKI1), which is derived from CEN.PK102-3A (MATA ura3-52 leu2-112).

During construction strains were maintained on complex (YP: 10 g/l yeast extract (BD Difco), 20 g/l peptone (BD Difco)) or synthetic medium (MY) [6] supplemented with glucose (2%) as carbon source (YPD or MYD) and 1.5% agar in the case of plates After transformation integrants were selected by plating on YPD containing Geneticin® (G418) (Invitrogen/GIBCO) at 200 µg/ml or hygromycin B (Roche Diagnostics GmbH, Mannheim, Germany) at 300 µg/ml.

After transformation with plasmids strains were plated on MYD. Transformations of yeast were done according to Gietz and Woods [7].

Plasmids were amplified in *Escherichia coli* strain XL-1 blue (Stratagene, La Jolla, Calif., USA). Transformation was performed according to Inoue et al. [8]. *E. coli* was grown on LB (Luria-Bertani) plates or in liquid TB (Terrific Broth) medium for the isolation of plasmids [5].

1.3. Strain Construction

For TAL1 and RKI1 integration of the TPI1 promoter 5' of the open reading frame was done by amplifying a PCR fragment with the KanMX marker and the TPI1 promoter and directing it to the target location via homologous ends. The PCR was performed with Taq DNA polymerase (Amersham Pharmacia, Piscataway, USA) according to the manufacturer's specifications. The template was pUG6$P_{TPI}$ with $P_{TAL}$disA and $P_{TAL}$disB or $P_{RKI}$disA and $P_{RKI}$disB (Table 3) as primers.

In the case of TKL1 and RPE1, plasmids pUG6$P_{TPI}$-TKL1 and pUG6$P_{TPI}$-RPE1 were linearized with PvuII and SalI respectively and integrated into the genome. Correct integration of the constructs was verified colony PCR with TAL1 intern+KanA for TAL1 and $P_{TPI}$ primer+"intern" for TKL1, RPE1, and RPI1. The "intern" primers anneal downstream of the integrated constructs, while $P_{TPI}$ primer anneals at the 3' end of the TPI1 promoter.

After integration of a construct the KanMX marker was removed with the cre recombinase. To this end strains were transformed with pSH47 [3]. Colonies with the plasmid were resuspended in YP with 1% galactose and incubated for 1 hour at 30° C. Then about 200 cells were plated on YPD. The resulting colonies were checked for loss of the KanMX marker and pSH47 (URA3).

In addition the GRE3 gene was replaced by the hphMX cassette from pAG32, conferring hygromycin resistance [9]. The hphMX cassette was amplified using oligo's 5' gre3:: Kanlox and 3' gre3::Kanlox. Correct integration was verified using by PCR with 5'GRE3+KanA and 3'GRE3+KanB (Table 3). KanA and KanB anneal to the *A. gossipi* TEF promoter and terminator respectively, while the other primers anneal outside of the GRE3 open reading frame.

Colony PCR was done with Taq DNA polymerase (Amersham Pharmacia, Piscataway, USA) according to the manufacturer's specifications. As template cells were resuspended in 2.5 µl 0.02M NaOH to which the PCR reaction mixture was added. The PCR was performed in a Biometra TGradient Thermocycler (Biometra, Göttingen, Germany) with the following settings: 30 cycles of 1 min annealing at 60° C., 3 min extension at 72° C. and 1 min denaturing at 94° C.

The resulting strain, RWB212 (MATA ura3-52 leu2-112 loxP-$P_{TPI}$::(−266,−1)TAL1 gre3::hphMX pUGP$_{TPI}$-TKL1 pUGP$_{TPI}$-RPE1 KanloxP-$P_{TPI}$:: (−?,−1)RKI1), was then transformed with pAKX002, a multicopy vector containing the *Piromyces* sp. E2 XylA behind the TPI1 promoter, as well as p415ADHXKS. Which gave us RWB217 (MATA ura3-52 leu2-112 loxP-$P_{TPI}$::(−266,−1)TAL1 gre3::hphMX pUGP$_{TPI}$-TKL1 pUGP$_{TPI}$-RPE1 KanloxP-$P_{TPI}$::(−?,−1) RKI1 {pAKX002, p415ADHXKS}).

1.4. Strain Maintenance

Stock cultures were grown at 30° C. in shake flasks on synthetic medium [6] supplemented with 20 g of glucose/l. When stationary phase was reached, sterile glycerol was added to 30% (vol/vol), and 2-ml aliquots were stored in sterile vials at −80° C.

1.5. Cultivation and Media

Shake-flask cultivation was performed at 30° C. in a synthetic medium [6]. The pH of the medium was adjusted to 6.0 with 2 M KOH prior to sterilization. Precultures were prepared by inoculating 100 ml medium containing 20 g/l xylose in a 500 ml shake-flask with a frozen stock culture. After 24 to 48 h incubation at 30° C. in an orbital shaker (200 rpm), this culture was used to inoculate either shake-flask cultures or fermenter cultures. The synthetic medium for anaerobic cultivation was supplemented with 0.01 g/l ergosterol and 0.42 g/l Tween 80 dissolved in ethanol [10,11], this resulted in 11-13 mM ethanol in the medium.

1.6. Anaerobic Batch Cultivation in Fermenters

Anaerobic batch cultures were carried out in 2-liter laboratory fermenters (Applikon, Schiedam, The Netherlands) equipped with Norprene tubing, with a working volume of 1.5 liters, at 30° C. and at pH 5.0. Cultures were stirred at 800 rpm and sparged with 0.5 l/min of high-grade nitrogen (<5 ppm oxygen). The synthetic medium was supplemented with the anaerobic growth factors ergosterol and Tween 80 (0.01 and 0.42 g/l, respectively) as well as 100 µl/l of silicone antifoam (BDH, Poole, UK).

1.7. Determination of Culture Dry Weight

Culture samples (10.0 ml) were filtered over preweighed nitrocellulose filters (pore size 0.45 µm; Gelman Laboratory, Ann Arbor, USA). After removal of medium the filters were washed with demineralized water and dried in a microwave oven (Bosch, Stuttgart, Germany) for 20 min at 360 W and weighed. Duplicate determinations varied by less than 1%.

1.8. Gas Analysis

Exhaust gas was cooled in a condensor (2° C.) and dried with a Permapure dryer type MD-110-48P-4 (Permapure, Toms River, USA). $O_2$ and $CO_2$ concentrations were determined with a NGA 2000 analyzer (Rosemount Analytical, Orrville, USA). Exhaust gas-flow rate and specific oxygen-consumption and carbon-dioxide production rates were determined as described previously [12,13]. In calculating these biomass-specific rates, a correction was made for volume changes caused by withdrawing culture samples.

1.9. Metabolite Analysis

Glucose, xylose, xylitol, organic acids, glycerol and ethanol were detected by HPLC analysis on a Waters Alliance 2690 HPLC (Waters, Milford, USA) containing a Biorad HPX 87H column (Biorad, Hercules, USA). The column was eluted at 60° C. with 0.5 g/l $H_2SO_4$ at a flow rate of 0.6 ml/min. Detection was by means of a Waters 2410 refractive-index detector and a Waters 2487 UV detector. Xylulose was determined enzymatically in the following manner. The reaction mixture consisted of 100 mM Tris-HCl buffer (pH7.5) with 10 mM $MgCl_2$, 0.30 mM NADH and an adequate amount of sample (1 ml total volume) the assay was started by the addition of 0.2 U sorbitol dehydrogenase (Sigma, St Louis, USA). The xylulose concentration was calculated using an absorption coefficient of 6.3 mM/cm for NADH.

1.10. Carbon Recoveries and Ethanol Evaporation

Carbon recoveries were calculated as carbon in products formed divided by the total amount of sugar carbon consumed and were based on a carbon content of biomass of 48%. To correct for ethanol evaporation during the fermentations, the amount of ethanol produced was assumed to be equal to the measured cumulative production of $CO_2$ minus the $CO_2$ production that occurred due to biomass synthesis (5.85 mmol $CO_2$ per gram biomass [14]) and the $CO_2$ associated with acetate formation as described previously [2].

1.11 Microarray Analysis

Sampling of cells from chemostats, probe preparation and hybridization to Affymetrix Genechip® microarrays were performed as described previously [15]. The results for each growth condition were derived from three independently cultured replicates.

1.12. Data Acquisition and Analysis

Acquisition and quantification of array images and data filtering were performed using the Affymetrix software packages: Microarray Suite v5.0, MicroDB v3.0 and Data Mining Tool v3.0.

Before comparison, all arrays were globally scaled to a target value of 150 using the average signal from all gene features using Microarray Suite v5.0. From the 9,335 transcript features on the YG-S98 arrays a filter was applied to extract 6,383 yeast open reading frames of which there were 6,084 different genes. This discrepancy was due to several genes being represented more than once when sub-optimal probe sets were used in the array design.

To represent the variation in triplicate measurements, the coefficient of variation (C.V.; standard deviation divided by the mean) was calculated as previously described by Boer et al. [16].

For further statistical analyses Microsoft Excel running the Significant Analysis of Microarrays (SAM v1.12) add in was used [17] for possible pair wise comparisons of the eight data sets. Genes were considered as being changed in expression if they were called significantly changed using SAM (expected median false-discovery rate (FDR) of 1%) by at least 2-fold from each other condition. Hierarchical clustering of the obtained sets of significantly changed expression levels was subsequently performed by Genespring (Silicon Genetics).

1.13 Enzyme Assays

Xylose isomerase activity was assayed at 37° C. in a reaction mixture containing 50 mM phosphate buffer (pH 7.0), 10 mM xylose, 10 mM $MgCl_2$ and a suitable amount of cell-free extract. The amount of xylulose formed was determined by the cysteine-carbazole method (9). Alternatively xylose isomerase activity was assayed at 30° C. enzyme assay as developed by Kersters-Hildersson et al. (Kinetic characterization of D-xylose isomerases by enzymatic assays using D-sorbitol dehydrogenase. *Enz. Microb. Technol.* 9 (1987) 145-148). The in vitro activity of xylose isomerase in the cell-free extracts of transformed *S. cerevisiae* strains is dependent on bivalent cations ($Mg^{2+}$ or $Co^{2+}$).

Xylulose kinase and xylose reductase activities were assayed as described by Witteveen et al. (28). One unit of activity is defined as the amount of enzyme producing 1 nmol of xylulose per min under the assay conditions. Xylulose formed was determined by the method of Dische and Borenfreund (Dische and Borenfreund, 1951, *J. Biol. Chem.* 192: 583-587) or by HPLC using a Biorad HPX-87N Column operated at 80° C. and eluted at 0.6 ml/min using 0.01 M $Na_2HPO_4$ as the eluent. Xylose and xylulose were detected by a Refractive Index detector at an internal temperature of 60° C.

Specific activity is expressed as units per mg protein. Protein was determined with the Bio-Rad protein reagent (Bio-Rad Laboratories, Richmond, Calif., USA) with bovine γ-globulin as a standard.

2. Results

2.1 Overexpression of the Pentose Phosphate Pathway (PPP) Genes

Previously we have shown that expressing a fungal xylose isomerase in *Saccharomyces cerevisiae* is in principle enough to allow anaerobic growth of this yeast on xylose as the sole carbon source provided that sufficient selective pressure is applied [2]. The selected strain still however, did not perform up to industrial requirements (Table 1).

In order to investigate the possibility of rate limiting steps in pentose phosphate metabolism it was decided to construct a strain overproducing all the enzymes required to convert xylose into fructose-6-phosphate and glyceraldehyde-3-phosphate. The overexpressed enzymes were: xylose isomerase (XI), xylulokinase (XKS), ribulose-5-phosphate isomerase (R5PI), ribulose-5-phosphate epimerase (R5PE), transketolase (TKT) and transaldolase (TAL). Additionally the non-specific aldose reductase encoded by GRE3, which mediates unwanted production of xylitol [18] was deleted. Since some of the substrates of the enzymes in the PPP are not commercially available it was decided to check for overexpression via DNA arrays rather than via enzyme activity measurements. The results listed in Table 1 further confirmed that the transcription of the target genes was successfully modified in strain RWB 212.

2 show that both sugars were completely consumed but glucose was the preferred substrate. Xylose consumption commenced after approximately 80% of the glucose was consumed.

3. Functional Expression of the *B. thetaiotaomicron* Xylose Isomerase in Yeast

The nucleotide sequence encoding the *B. thetaiotaomicron* VPI-5482 xylose isomerase (Acc. No.'s AA075900 or NP 809706; SEQ ID NO. 10) was cloned into a multicopy yeast expression vector to give p426GPDBtXI. This plasmid was used to transform RWB215 (MATα ura3-52 leu2-112loxP-PTPI::(−266,−1)TAL1 gre3::hphMX pUGP$_{TPI}$-TKL1

TABLE 1 mRNA levels of structural genes encoding xylulokinase and pentose-phosphate-pathway enzymes in the reference strain *S. cerevisiae* CEN.PK113-7D and in the engineered, xylose-isomerase-expressing strain *S. cerevisiae* RWB212.

| Gene | Systematic name | Enzyme name | Transcript level CEN.PK113-7D | Transcript level RBW212 | Fold-change Mutant vs WT |
|---|---|---|---|---|---|
| XylA | | xylose isomerase | n.d. | n.d. | |
| XKS1 | YGR194C | Xylulokinase | 91 ± 7 | 321 ± 54 | +3.5 |
| TAL1 | YLR354C | Transaldolase | 574 ± 49 | 959 ± 91 | +1.7 |
| TKL1 | YPR074C | transketolase 1 | 450 ± 37 | 1982 ± 79 | +4.4 |
| RPE1 | YJL121C | D-ribulose-5-phosphate 3-epimerase | 299 ± 24 | 2551 ± 385 | +8.5 |
| RKI1 | YOR095C | D-ribose-5-phosphate ketol-isomerase | 96 ± 8 | 483 ± 64 | +5.0 |
| GRE3 | YHR104w | aldose reductase | 322 ± 6 | 12 ± 0 | −26.8 |
| ACT1 | YFL039C | Actin | 408 ± 32 | 366 ± 56 | NC$^a$ |
| PDA1 | YER178W | E1α subunit of pyruvate dehydrogenase complex | 2901 ± 142 | 3217 ± 182 | NC | n.d. = not determined (not represented on Affymetrix microarrays);
$^a$NC = not changed.

Both strains were grown in aerobic, glucose-limited chemostat cultures (D=0.10 h$^{-1}$). Transcript levels were determined with Affymetrix GeneChip microarrays. Data are the average±average deviation of the mean of analyses on three independent cultures for each strain. ACT1 (Ng and Abelson, 1980, *Proc. Nat. Acad. Sci. USA.* 77:3912-3916) and PDA1 (Wenzel et al., 1995, *Nucleic. Acids Res.* 23:883-884) are included as internal standards.

2.2 Physiological Characterization of the Engineered Strain

One of the striking properties of the engineered strain was its ability to grow anaerobically on xylose (FIG. 1) without any selective pressure being required. Anaerobic growth on xylose in mineral medium proceeded with a growth rate as high as 0.09 h$^{-1}$. Xylulose was not accumulated but xylitol formation, though extremely small, was detectable (FIG. 1) biomass, ethanol and glycerol yields of stain RWB 212 on xylose were comparable to those of RWB 202-AFX which was obtained via evolutionary engineering (Table 2). From Table 2 a specific xylose consumption rate of more than 1.0 g xylose/g biomass/h can be calculated (Qs=0.09/0.085=1,059 gram Xyl/gram X/h), compared to 345 mg xylose/g biomass/h for RWB 202-AFX while a yield at least similar to the yield on glucose was obtained.

2.3 Mixed Substrate Utilization

As pointed out in the introduction: economic conversion of hemicellulose hydrolysates to ethanol requires the fermentation of both glucose and xylose, preferably simultaneously. In order to verify the properties of strain RWB 212 with respect to mixed sugar utilization, the yeast was grown in a mixture of glucose and xylose (20 g/l each). The results depicted in FIG.

pUGP$_{TPI}$-RPE1 KanloxP-P$_{TPI}$::(−?,−1)RKI1), which was further transformed with p415ADHXKS for overexpression of xylulokinase. Two independent transformants were picked and both were able to grow on minimal medium with xylose as sole carbon source and in lysates of the transformants a specific xylose isomerase activity of 140+/−20 U per mg protein was measured, compared to about 1300 U per mg protein for the strains expressing the *Piromyces* xylose isomerase.

4. Selection of RWB 212

Figure 3A:
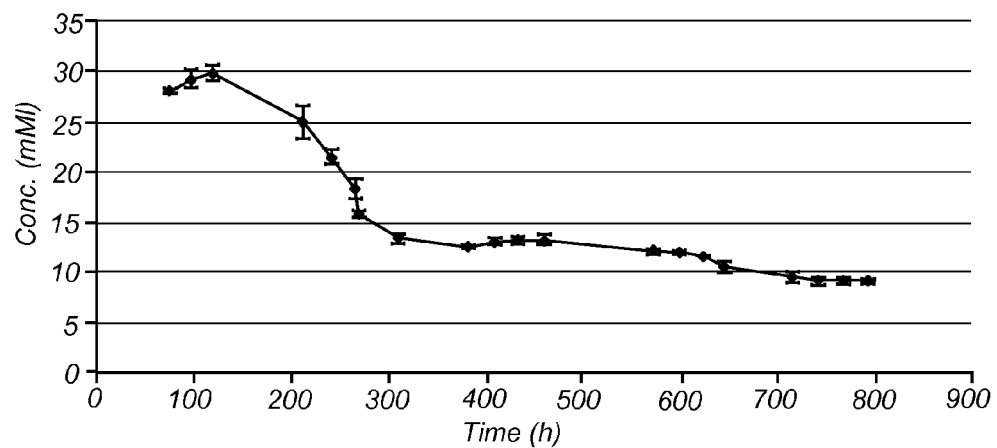
Figure 3B:
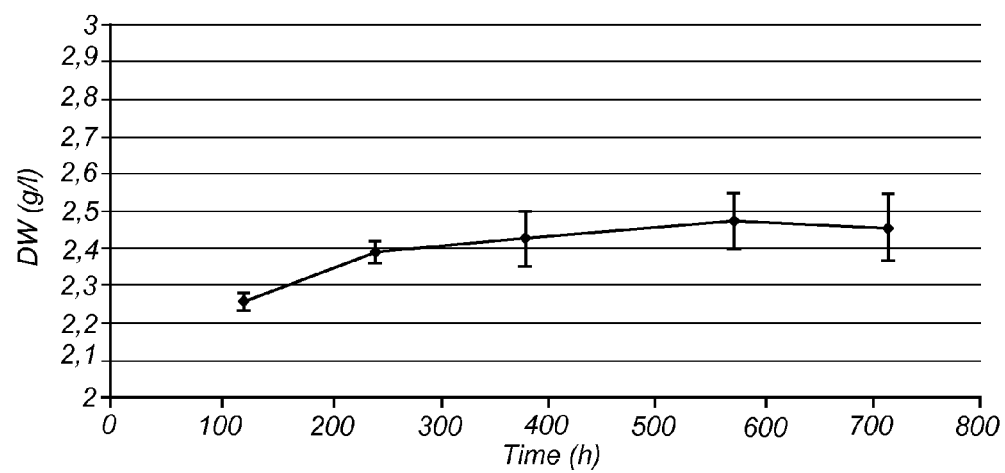

The strain RWB 212 (see above) was placed under selective pressure by cultivation in anaerobic chemostat cultures (duplo) with 30 g/l xylose as the carbon source with an estimated growth rate of 0.06 h$^{-1}$. The selection process was monitored by determination of culture dry weight and residual xylose concentration. The initial residual xylose concentration was around 30 mM but already after 26 generations (300 hours) residual xylose concentrations had decreased to less than 15 mM (FIG. 3A) and a corresponding increase in biomass concentration was also observed (FIG. 3B).

From these chemostat cultures samples were taken at 530 hours and these were plated on mineral medium agar plates supplemented with 2% glucose. After 62 hours at 30° C. single colonies from these plates were restreaked on fresh glucose plates. After another 72 hours incubation at 30° C., two colonies were selected (one colony originating from each separate chemostat) and used to inoculate precultures (aerobic shake flasks, mineral medium with glucose) for anaerobic fermentor batches on 20 g/l glucose and 20 g/l xylose.

Figure 4:
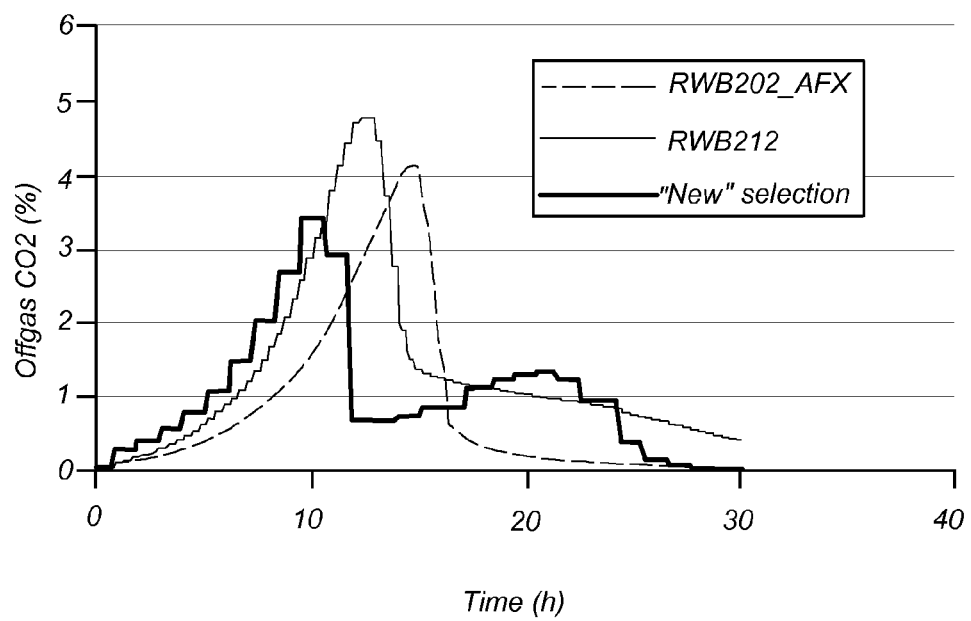
Figure 5A:
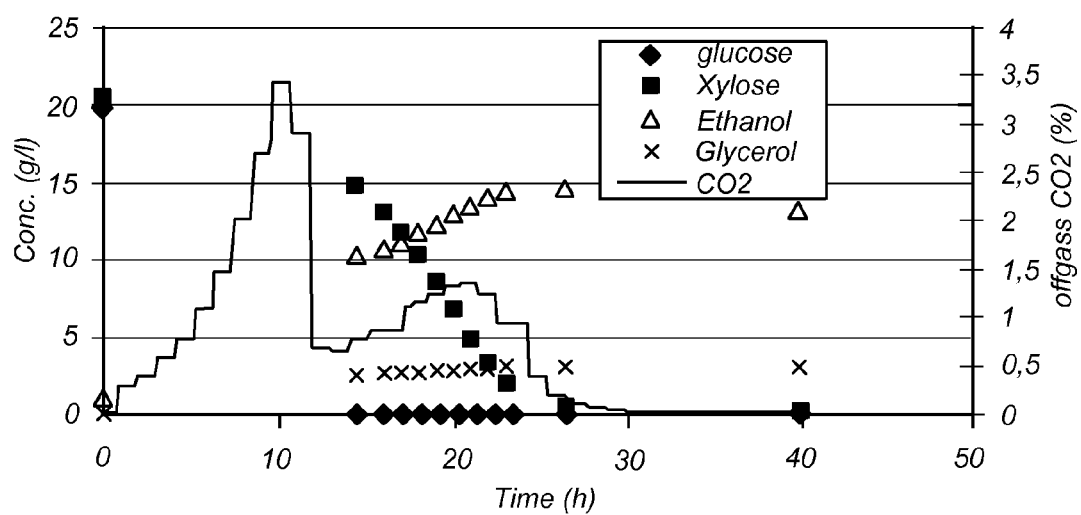
Figure 5B:
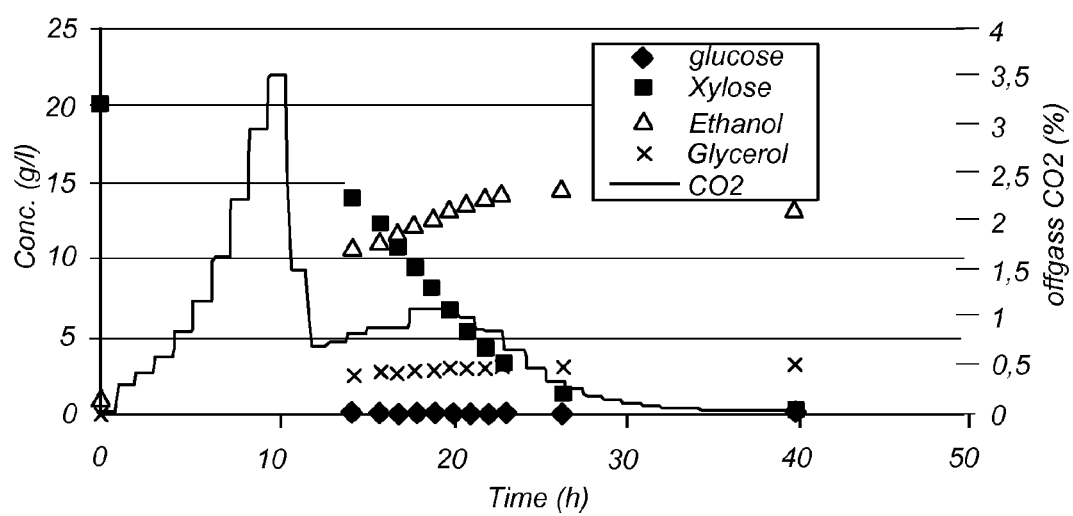

From the $CO_2$ off-gas signals in FIG. 4 it is evident that these cultures have superior xylose utilization characteristics compared to the parental strain RWB 212 and the other selection strain RWB 202-AFX. The "new" selection strain displays an increase in $CO_2$ production rate when consuming xylose, which is not observed in the parental strain. FIG. 5 depicts the measured concentrations of carbon source and products in supernatants of these two independent batches, mainly during the xylose consumption phase. The overall (i.e., glucose+xylose phase) volumetric ethanol production rate of both experiments is higher than 0.5 g/L/hr and the first batch also demonstrates a volumetric productivity in the xylose consumption phase of higher than 0.5 g/L/hr.

5. Testing of Strains RWB 204, 206, 208 and 210

The strains tested have been constructed as has been described in the patent text as well as in Kuyper et al., 2005, *FEMSYR* 5:399-409. The modified genes are listed in the Table below:
Listing of the Genes Overexpressed and Deleted in the Used Strains

| Strain | Overexpression | Deletion |
|---|---|---|
| RWB 204 | TAL1 | |
| RWB 206 | TAL1 | gre3 |
| RWB 208 | TAL1, TKL1 | gre3 |
| RWB 210 | TAL1, TKL1, RPE1 | gre3 |
| RWB 212 | TAL1, TKL1, RPE1, RKI1 | gre3 |

After the introduction of the modifications listed in the above Table all strains were transformed with two plasmids; pAKX002 expressing the *Piromyces* xylose isomerase and p415ADHXKS a second plasmid expressing the endogenous xylulokinase. In the above article RWB 212 transformed with the two plasmids was given a separate number: RWB 217. A repeat of the transformation of RWB 212 with the two plasmids resulted in RWB 223.

After transformation single colonies were streaked on synthetic medium agar plates with glucose. From these plates shake flask cultures with synthetic medium and 20 g/l xylose were inoculated and incubated at 30'C for 48 hours. Each shake flask culture was used to inoculate an anaerobic fermentor with synthetic medium and 20 g/l xylose.

After 48 hours incubation the shake flask inoculated with RWB 204 had not grown as determined by visual inspection. All four flasks were used to inoculate one fermentor. The growth in the fermentors was monitored by measuring the $CO_2$ concentrations in off gas.

Figure 1B:
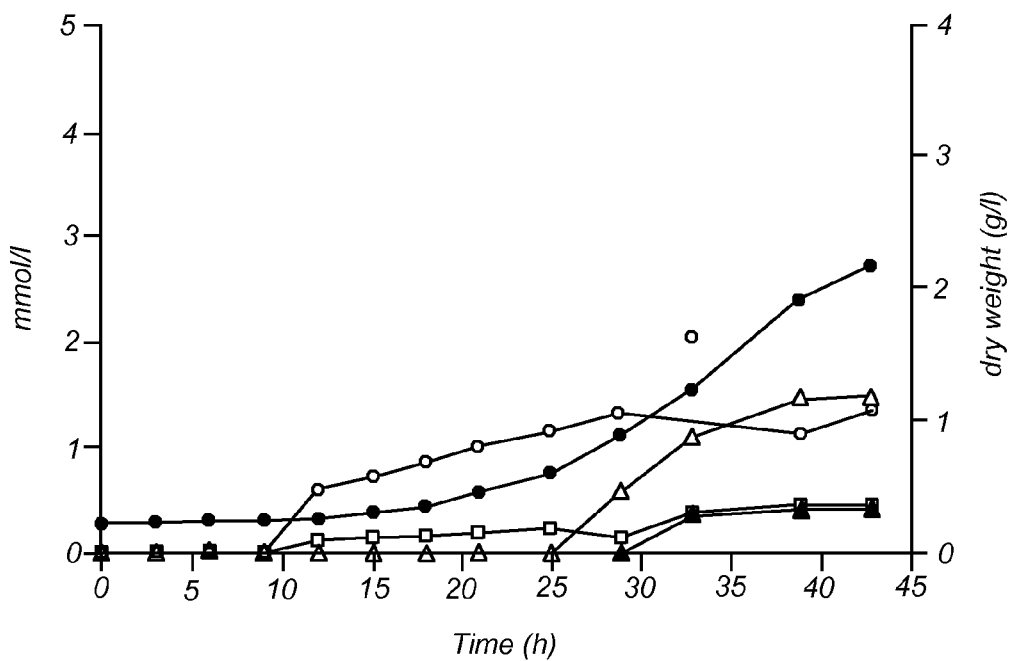
Figure 2A:
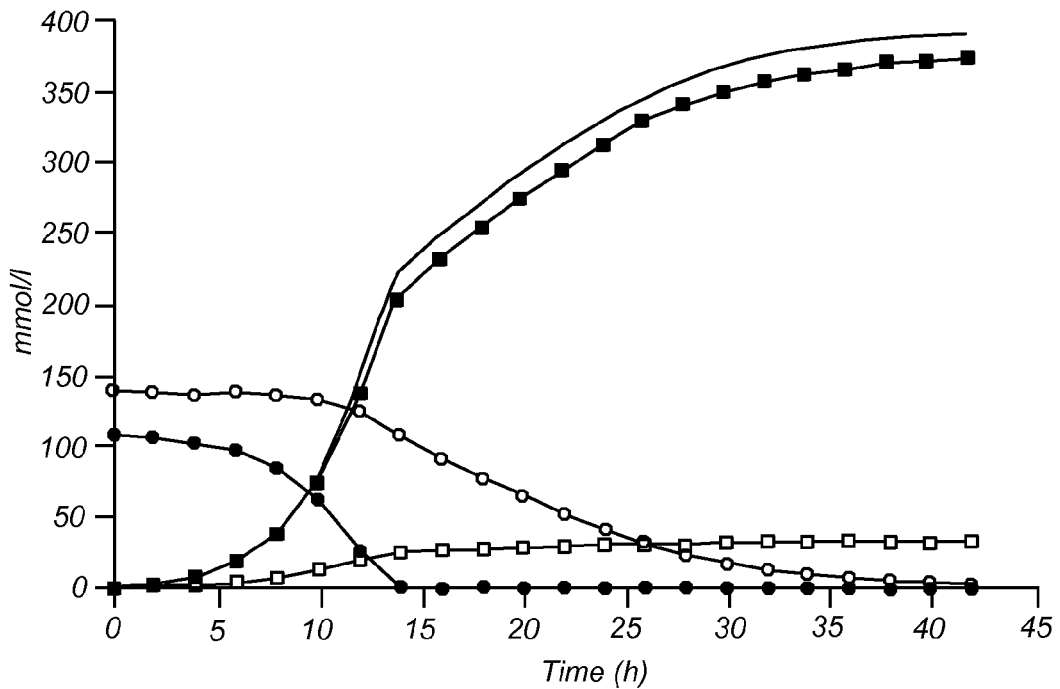
Figure 2B:
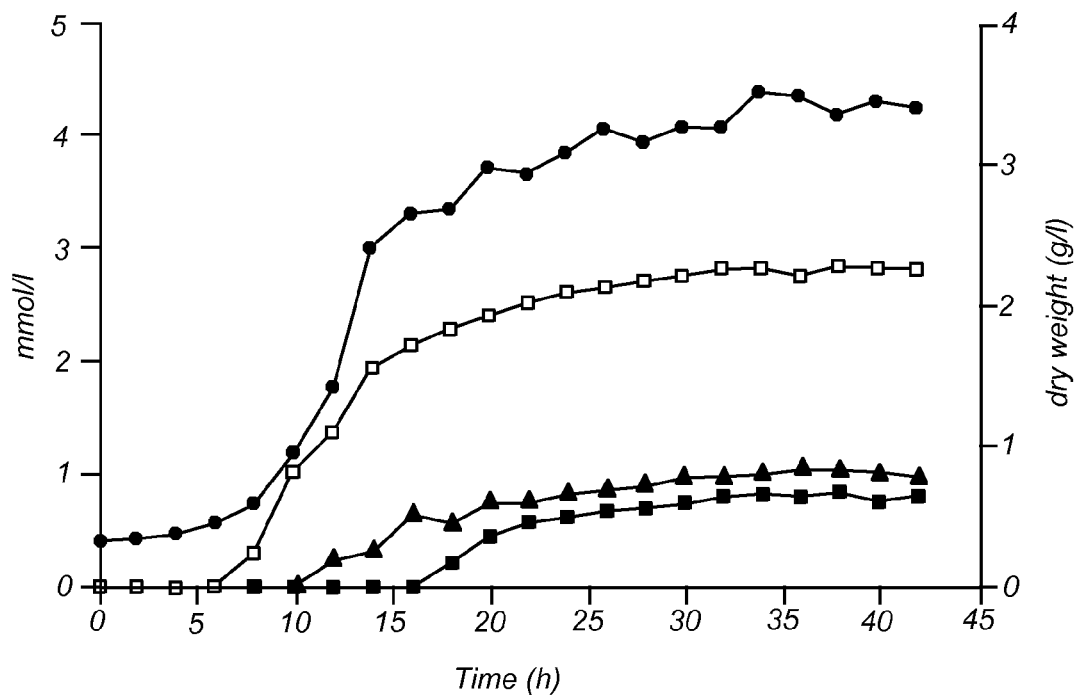

For reference purposes the $CO_2$ profiles of RWB 217 and RWB 223 (both with TAI, TKL, RPE and RKI overexpression) are also given in FIG. 1. Over a period of 100 hours no significant $CO_2$ production could be measured in the off gas of the batches with RWB 204 and RWB 206. The growth rate determined from these $CO_2$ production graphs is 0.12 $h^{-1}$ for RWB 208, 217 and 223, for RWB 210 it was determined at 0.08 $h^{-1}$. From these result follows that overexpression of both transaldolase and transketolase are required for anaerobic growth on xylose. Furthermore, the additional overexpression of ribose 5-phosphate epimerase in RWB 210 decreases the growth rate on xylose. The overexpression of RPE1 probably disturbs the equilibrium between xylulose-5P, ribulose-5P and ribose-5P, hindering the activity of transketolase. Under these experimental conditions the additional overexpression of the R5P-epimerase and -isomerase does not further improve the performance of anaerobic xylose fermentation.

TABLE 2

Growth parameters, sugar consumption and product formation by the wild-type CEN.PK 113-7D, the selected strain RWB 202-AFX and the engineered strain RWB 212 during anaerobic batch cultivation in fermenters.

| | CEN.PK 113-7D | RWB 202-AFX | RWB 202-AFX | RWB 212 | RWB 212 |
|---|---|---|---|---|---|
| Carbon source (w/v) | Glucose (2%) | Glucose (2%) | Xylose (2%) | Xylose (2%) | Glucose (2%) + Xylose (2%) |
| Specific growth rate (hr$^{-1}$) | 0.34 ± 0.00 | 0.24 ± 0.00 | 0.03 ± 0.00 | 0.09 ± 0.00 | 0.25 ± 0.00$^a$ |
| Biomass yield (g/g) | 0.099 ± 0.003 | 0.079 ± 0.000 | 0.088 ± 0.004 | 0.085 ± 0.002 | 0.074 ± 0.001 |
| Ethanol yield$^b$ (g/g) | 0.40 ± 0.01 | 0.40 ± 0.00 | 0.42 ± 0.00 | 0.43 ± 0.00 | 0.43 ± 0.00 |
| Carbon recovery$^b$ (%) | 104.0 ± 1.1 | 103.7 ± 0.8 | 105.5 ± 0.0 | 105.9 ± ?? | 103.2 ± ?? |
| Sugar consumed (mM) | 116.1 ± 0.3 | 114.9 ± 0.4 | 137.4 ± 0.2 | 133.9 ± 0.1 | 108.5 ± 0.2 + 136.0 ± 0.3 |
| Products: | | | | | |
| Biomass (g/l) | 2.07 ± 0.06 | 1.64 ± 0.01 | 1.81 ± 0.08 | 1.70 ± 0.04 | 2.97 ± 0.04 |
| $CO_2$ (mmoles/l) | 197.1 ± 3.4 | 196.9 ± 1.3 | 199.7 ± 1.5 | 199.9 ± 1.5 | 391.6 ± 0.6 |
| Ethanol$^c$ (mM) | 181.6 ± 3.9 | 180.3 ± 1.4 | 186.8 ± 2.2 | 188.5 ± 1.3 | 370.7 ± 0.4 |
| Xylitol (mM) | <0.01 | <0.01 | 2.76 ± 0.03 | 0.38 ± 0.04 | 0.78 ± 0.00 |
| Xylulose (mM)$^d$ | <0.01 | <0.01 | 7.98 ± 0.09 | <0.01 | <0.01 |
| Glycerol (mM) | 22.9 ± 0.2 | 24.2 ± 0.1 | 18.3 ± 0.3 | 17.8 ± 0.2 | 32.7 ± 0.3 |
| Acetate (mM) | 3.42 ± 0.11 | 6.93 ± 0.02 | 2.26 ± 0.16 | 1.40 ± 0.07 | 3.54 ± 0.02 |
| Succinate (mM) | 0.26 ± 0.01 | 0.27 ± 0.02 | 0.75 ± 0.00 | 0.39 ± 0.02 | 0.96 ± 0.00 |
| Lactate (mM) | 1.70 ± 0.02 | 1.49 ± 0.02 | 0.95 ± 0.02 | 1.46 ± 0.01 | 2.78 ± 0.03 |

Values are presented as the average and experimental deviation of two independent batch cultivations.

$^a$determined from the glucose consumption phase.

$^b$calculation based on the ethanol concentrations deduced from the $CO_2$ production, see Section 1.10.

$^c$deduced from the $CO_2$ production, see Section 1.10.

$^d$transient accumulation. This value represents the highest concentration during the mid-log phase. At the end of growth all xylulose had been reconsumed, in all other cultures the xylulose concentration remained below the detection limit.

TABLE 3

Primers used

| Oligo name | Sequence |
|---|---|
| P$_{TAL}$disA | CCTTTCCAACGAATCGTATATACTAACATGCGCGCGCTTCCTATGCAT AGGCCACTAGTGGATCTG |
| P$_{TAL}$disB | AGAGAGTTGTTAGCAACCTTTTGTTTCTTTTGAGCTGGTTCAGACATG GTGAATTCCTGTATGTG |
| 5'TAL1 | CTGACTGAGCCATATTGAGG |
| TAL1 intern | CACCAGTGTCGGCAACAACG |
| P$_{RKI}$disA | TCTTGTAGAAAATTAACAACATCGTGTTACATAAACTTGGTTACGCAT AGGCCACTAGTGGATCTG |
| P$_{RKI}$disB | TTGCCCAAAGATTCTAACGCATCAATTTTTGGGACACCGGCAGCCATG GTGAATTCCTGTATGTG |
| RKI1intern | CAGCTCTCTTGGCATCCTCC |
| EcoRI-5'TKL1 | GGAATTCATGACTCAATTCACTGACATTG |
| 3'TKL1-XhoI | GGCCTCGAGCTTGAATGGTGTGATTCTCT |
| TKL1intern | CCGCCATTGGTGATCTACAG |
| EcoRI-5'RPEI | GGAATTCATGGTCAAACCAATTATAGC |
| 3'RPEI-XhoI | CCGCTCGAGTTAGGCACTTACGTATCTTG |
| RPE1intern | GGAAGCCTTATGGAGTGTCA |
| P$_{TPI1}$primer | TGGCATGTGAGATTCTCCGA |
| KanA | CGCACGTCAAGACTGTCAAG |
| KanB | TCGTATGTGAATGCTGGTCG |
| 5'gre3::Kanlox | AAAATACTGTAATATAAATCGTAAAGGAAAATTGGAAATTTTTTCAGC TGAAGCTTCGTACGC |
| 3'gre3::Kanlox | TGGATTTTACTGGCTGGATCAGGCAAAAGTGGGGAATTTACCGCATAG GCCACTAGTGGATCTG |
| 5'GRE3 | CCTGGTGGAACATCCTAGAA |
| 3'GRE3 | GGATGACACCACAGGCAGAA |
| SpeI-5'XKS1 | GACTAGTATGTTGTGTTCAGTAATTCAG |
| 3'XKS1-SalI | TGCAGTCGACATTTTAGATGAGAGTCTTTTCC |

TABLE 4

Plasmids used

| | | |
|---|---|---|
| pUG6 | loxP-KanMX-loxP cassette | Guldener et al. [3] |
| pUG6P$_{TPI1}$ | pUG6 with the TPI1 promoter | present document |
| pUG6$_{TPI1}$-RPE1 | pUG6 with RPE1 behind theTPI1 promoter | present document |
| pUG6$_{TPI1}$-TKL1 | pUG6 with TKL1 behind the TPI1 promoter | present document |
| pAG32 | loxP-hphMX-loxP cassette | Goldstein et al. [9] |
| PAKX002 | 2μ, URA3, *Piromyces* XylA behind the TPI1 promoter | Kuyper et al. [20] |
| P415ADH | CEN, LEU2, ADH1 promoter | Mumberg et al. [21] |
| p415ADHXKS1 | CEN, LEU2, P$_{ADH1}$-XKS1 | present document |
| PSH47 | CEN, URA3, Cre recombinase behind P$_{GAL1}$ | Guldener et al..[3] |

REFERENCES

1. Bruinenberg, P. M., De Bot, P. H. M, Van Dijken, J. P. and Scheffers, W. A. (1983) The role of the redox balance in the anaerobic fermentation of xylose by yeasts. Eur. J. Appl. Microbiol. Biotechnol. 18, 287-292.

2. Kuyper, M., Winkler, A. A., Van Dijken, J. P. and Pronk, J. T. (2004) Minimal metabolic engineering of *Saccharomyces cerevisiae* for efficient anaerobic xylose fermentation: a proof of principle. FEMS Yeast Res. 4, 655-664.

3. Guldener, U., Heck, S., Fiedler, T., Beinhauer, J. and Hegemann, J. H. (1996) A new efficient gene disruption cassette for repeated use in budding yeast. Nucleic Acids Res. 24, 2519-2524.
4. Mumberg, D., Muller, R. and Funk, M. (1995) Yeast Vvectors for the controlled expression of heterologous proteins in different genetic backgrounds. Gene 156, 119-122.
5. Sambrook, K., Fritsch, E. F. and Maniatis, I. (1989) Molecular Cloning: A Laboratory Manual, 2$^{nd}$ ed., Cold Spring Harbor Press, New York.
6. Verduyn, C., Postma, E., Scheffers, W. A. and Van Dijken, J. P. (1992) Effect of benzoic acid on metabolic fluxes in yeasts: a continuous-culture study on the regulation of respiration and alcoholic fermentation. Yeast 8, 501-517.
7. Gietz, R. D. and Woods, R. A. (2002) Transformation of yeast by lithium acetate/single-stranded carrier DNA/polyethylene glycol method. Methods Enzymol. 350, 87-96.
8. Inoue, H., Nojima, H. and Okayama, H. (1990) High efficiency transformation of Escherichia coli with plasmids. Gene 96, 23-28.
9. Goldstein, A. L. and McCusker, J. H. (1999) Three new dominant drug resistance cassettes for gene disruption in Saccharomyces cerevisiae. Yeast 15, 1541-1553.
10. Andreasen, A. A. and Stier, T. J. (1953) Anaerobic nutrition of Saccharomyces cerevisiae. I. Ergosterol requirement for growth in a defined medium. J. Cell Physiol. 41, 23-36.
11. Andreasen, A. A. and Stier, T. J. (1954) Anaerobic nutrition of Saccharomyces cerevisiae. II. Unsaturated fatty acid requirement for growth in a defined medium. J. Cell Physiol. 43, 271-281.
12. Van Urk, H., Mak, P. R., Scheffers, W. A. and Van Dijken, J. P. (1988) Metabolic responses of Saccharomyces cerevisiae CBS 8066 and Candida utilis CBS 621 upon transition from glucose limitation to glucose excess. Yeast 4, 283-291.
13. Weusthuis, R. A., Luttik, M. A., Scheffers, W. A., Van Dijken, J. P. and Pronk, J. T. (1994) Is the Kluyver effect in yeasts caused by product inhibition? Microbiology 140, 1723-1729.
14. Verduyn, C., Postma, E., Scheffers, W. A. and Van Dijken, J. P. (1990) Physiology of Saccharomyces cerevisiae in anaerobic glucose-limited chemostat cultures. J. Gen. Microbiol. 136, 395-403.
15. Piper, M. D., Daran-Lapujade, P., Bro, C., Regenberg, B., Knudsen, S., Nielsen, J. and Pronk, J. T. (2002) Reproducibility of oligonucleotide microarray transcriptome analyses. An interlaboratory comparison using chemostat cultures of Saccharomyces cerevisiae. J. Biol. Chem. 277, 37001-37008.
16. Boer, V. M., de Winde, J. H., Pronk, J. T. and Piper, M. D. (2003) The genome-wide transcriptional responses of Saccharomyces cerevisiae grown on glucose in aerobic chemostat cultures limited for carbon, nitrogen, phosphorus, or sulfur. J. Biol. Chem. 278, 3265-3274.
17. Tusher, V. G., Tibshirani, R. and Chu, G. (2001) Significance analysis of microarrays applied to the ionizing radiation response. Proc. Natl. Acad. Sci. U.S.A 98, 5116-5121.
18. Träff, K. L., Otero Cordero, R. R., Van Zyl, W. H. and Hahn-Hägerdal, B. (2001) Deletion of the GRE3 aldose reductase gene and its influence on xylose metabolism in recombinant strains of Saccharomyces cerevisiae expressing the xylA and XKS1 genes. Appl. Environ. Microbiol. 67, 5668-5674.
19. Jeffries, T. W. and Jin, Y. S. (2004) Metabolic engineering for improved fermentation of pentoses by yeasts. Applied Microbiology and Biotechnology 63, 495-509.
20. Kuyper, M., Harhangi, H. R., Stave, A. K., Winkler, A. A., Jetten, M. S., De Laat, W. T., D Ridder, J. J., Op den Camp, H. J., Van Dijken, J. P. and Pronk, J. T. (2003) High-level functional expression of a fungal xylose isomerase: the key to efficient ethanolic fermentation of xylose by Saccharomyces cerevisiae? FEMS Yeast Res. 4, 69-78.
21. Mumberg, D., Muller, R. and Funk, M. (1995) Yeast Vvectors for the controlled expression of heterologous proteins in different genetic backgrounds. Gene 156, 119-122.

What is claimed is:

1. A yeast or filamentous fungal host cell transformed with a nucleic acid construct comprising a nucleotide sequence that encodes a xylose isomerase enzyme comprising an amino acid sequence that has at least 85% sequence identity with the amino acid sequence SEQ ID NO:2, which construct, upon transformation of the host cell, confers on the host cell the ability to directly isomerize xylose to xylulose, and wherein the host cell comprises a genetic modification that
   (a) increases the flux of the pentose phosphate pathway, and
   (b) results in overexpression of at least one gene of the non-oxidative branch of the pentose phosphate pathway.

2. The host cell according to claim 1, wherein the nucleotide sequence encodes a xylose isomerase enzyme that is obtainable from a bacterium of the class Bacteroides.

3. The host cell according to claim 1, wherein the nucleotide sequence is adapted to optimize its codon usage to that of the host cell.

4. The host cell according to claim 1, wherein the gene of the non-oxidative branch of the pentose phosphate pathway is selected from the group consisting of the gene encoding
   (i) ribulose-5-phosphate isomerase,
   (ii) ribulose-5-phosphate epimerase,
   (iii) transketolase and
   (iv) transaldolase.

5. The host cell according to claim 4, wherein the at least one gene that is overexpressed encodes a transketolase or a transaldolase.

6. The host cell according to claim 1, wherein the at least one gene that is overexpressed is endogenous to the host cell.

7. The host cell according to claim 1, wherein the host cell further comprises a genetic modification that increases specific xylulose kinase enzymatic activity.

8. The host cell according to claim 7, wherein the further genetic modification comprises overexpression of the gene encoding said xylulose kinase.

9. The host cell according to claim 8, wherein the overexpressed xylulose kinase gene is endogenous to the host cell.

10. A host cell according to claim 1, wherein the host cell further comprises a genetic modification that reduces nonspecific aldose reductase activity in the cell.

11. The host cell according to claim 10, wherein the reduced activity results from reduced expression of or inactivation of a gene encoding nonspecific aldose reductase.

12. The host cell according to claim 11, wherein the nonspecific aldose reductase gene is inactivated by (i) deletion of at least part of the gene or (ii) disruption of the gene.

13. The host cell according to claim 11, wherein (i) expression of each gene in the host cell that encodes a nonspecific aldose reductase is reduced or (ii) each gene that encodes a nonspecific aldose reductase is inactivated.

14. The host cell according to claim 1 that is a yeast cell.

15. The yeast cell according to claim 14 that is a member of one of the following genera: *Saccharomyces, Kluyveromyces, Candida, Pichia, Schizosaccharomyces, Hansenula, Kloeckera, Schwanniomyces,* or *Yarrowia*.

16. The yeast cell according to claim 14 that is a member of one of the following species: *S. cerevisiae, S. bulderi, S. barnetti, S. exiguus, S. uvarum, S. diastaticus, K. lactis, K. marxianus,* or *K. fragilis*.

17. The host cell according to claim 1 that is a filamentous fungus.

18. The filamentous fungus according to claim 17 that is a member of one of the following genera: *Aspergillus, Trichoderma, Humicola, Acremonium, Fusarium,* or *Penicillium*.

19. The host cell according to claim 1, that expresses one or more enzymes that confers on the host cell the ability to produce at least one fermentation product selected from the group consisting of ethanol, lactic acid, 3-hydroxypropionic acid, acrylic acid, acetic acid, succinic acid, citric acid, an amino acid, 1,3-propane-diol, ethylene, glycerol, a β-lactam antibiotic and a cephalosporin.

20. A process for producing ethanol, comprising the steps of:
   (a) fermenting a medium containing a source of xylose with the modified host cell according to claim 1 that ferments xylose to ethanol, and, optionally,
   (b) recovering of the ethanol from the medium.

21. The process according to claim 20, wherein the medium also contains a source of glucose.

22. The process according to claim 20, wherein volumetric ethanol productivity is at least 0.5 g ethanol per liter per hour.

23. The process according to claim 20, wherein ethanol yield is at least 50%.

24. A fermentation process for producing one of the following products: lactic acid, 3-hydroxypropionic acid, acrylic acid, acetic acid, succinic acid, citric acid, an amino acid, 1,3-propane-diol, ethylene, glycerol, a β-lactam antibiotic and a cephalosporin, which process comprises the steps of:
   (a) fermenting a medium containing a source of xylose with the modified host cell according to claim 1 that ferments xylose to the product, and, optionally,
   (b) recovering the product from the medium.

25. The process according to claim 24, wherein the medium also contains a source of glucose.

* * * * *

SEQUENCE LISTING

```
<160> NUMBER OF SEQ ID NOS: 18

<210> SEQ ID NO 1
<211> LENGTH: 437
<212> TYPE: PRT
<213> ORGANISM: Piromyces sp.
<220> FEATURE:
<221> NAME/KEY: misc_feature
<223> OTHER INFORMATION: xylose isomerase

<400> SEQUENCE: 1

Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
                20                  25                  30

Glu Val Met Gly Lys Lys Met Lys Asp Trp Leu Arg Phe Ala Met Ala
            35                  40                  45

Trp Trp His Thr Leu Cys Ala Glu Gly Ala Asp Gln Phe Gly Gly Gly
        50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95
```

```
Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
            420                 425                 430

Val Ala Met Tyr Gln
        435

<210> SEQ ID NO 2
<211> LENGTH: 438
<212> TYPE: PRT
<213> ORGANISM: Bacteroides thetaiotaomicron
<220> FEATURE:
<221> NAME/KEY: misc_feature
<223> OTHER INFORMATION: xylose isomerase

<400> SEQUENCE: 2

Met Ala Thr Lys Glu Phe Phe Pro Gly Ile Glu Lys Ile Lys Phe Glu
1               5                   10                  15
```

Gly Lys Asp Ser Lys Asn Pro Met Ala Phe Arg Tyr Tyr Asp Ala Glu
            20                  25                  30

Lys Val Ile Asn Gly Lys Lys Met Lys Asp Trp Leu Arg Phe Ala Met
        35                  40                  45

Ala Trp Trp His Thr Leu Cys Ala Glu Gly Asp Gln Phe Gly Gly
 50                  55                  60

Gly Thr Lys Gln Phe Pro Trp Asn Gly Asn Ala Asp Ala Ile Gln Ala
 65                  70                  75                  80

Ala Lys Asp Lys Met Asp Ala Gly Phe Glu Phe Met Gln Lys Met Gly
                85                  90                  95

Ile Glu Tyr Tyr Cys Phe His Asp Val Asp Leu Val Ser Glu Gly Ala
            100                 105                 110

Ser Val Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Glu Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Thr Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
        355                 360                 365

Leu Glu Ser Ala Ala Ala Leu Leu Asp Glu Ser Pro Tyr Lys Lys Met
    370                 375                 380

Leu Ala Asp Arg Tyr Ala Ser Phe Asp Gly Gly Lys Gly Lys Glu Phe
385                 390                 395                 400

Glu Asp Gly Lys Leu Thr Leu Glu Asp Val Val Ala Tyr Ala Lys Thr
                405                 410                 415

Lys Gly Glu Pro Lys Gln Thr Ser Gly Lys Gln Glu Leu Tyr Glu Ala
            420                 425                 430

```
Ile Leu Asn Met Tyr Cys
        435

<210> SEQ ID NO 3
<211> LENGTH: 600
<212> TYPE: PRT
<213> ORGANISM: Saccharomyces cerevisiae
<220> FEATURE:
<221> NAME/KEY: misc_feature
<223> OTHER INFORMATION: xylulokinase

<400> SEQUENCE: 3

Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Val Gly His Leu Val Glu
    210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
                245                 250                 255

Asp Lys Thr Ile Arg Gln Lys Leu Met Arg Ala Pro Met Lys Asn Leu
            260                 265                 270

Ile Ala Gly Thr Ile Cys Lys Tyr Phe Ile Glu Lys Tyr Gly Phe Asn
        275                 280                 285

Thr Asn Cys Lys Val Ser Pro Met Thr Gly Asp Asn Leu Ala Thr Ile
    290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
                325                 330                 335

Tyr His Leu Phe Ile His Pro Thr Leu Pro Asn His Tyr Met Gly Met
            340                 345                 350
```

```
Ile Cys Tyr Cys Asn Gly Ser Leu Ala Arg Glu Arg Ile Arg Asp Glu
            355                 360                 365

Leu Asn Lys Glu Arg Glu Asn Asn Tyr Glu Lys Thr Asn Asp Trp Thr
    370                 375                 380

Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
                405                 410                 415

Ile Asn Lys Arg Val Ile Phe Asn Pro Lys Thr Gly Met Ile Glu Arg
            420                 425                 430

Glu Val Ala Lys Phe Lys Asp Lys Arg His Asp Ala Lys Asn Ile Val
                435                 440                 445

Glu Ser Gln Ala Leu Ser Cys Arg Val Arg Ile Ser Pro Leu Leu Ser
            450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
                485                 490                 495

Pro Glu Arg Thr Phe Phe Val Gly Gly Ala Ser Lys Asn Asp Ala Ile
            500                 505                 510

Val Lys Lys Phe Ala Gln Val Ile Gly Ala Thr Lys Gly Asn Phe Arg
            515                 520                 525

Leu Glu Thr Pro Asn Ser Cys Ala Leu Gly Gly Cys Tyr Lys Ala Met
    530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
                565                 570                 575

Val Asp Asn Glu Asn Trp Asp Arg Tyr Asn Ser Lys Ile Val Pro Leu
            580                 585                 590

Ser Glu Leu Glu Lys Thr Leu Ile
            595                 600

<210> SEQ ID NO 4
<211> LENGTH: 258
<212> TYPE: PRT
<213> ORGANISM: Saccharomyces cerevisiae
<220> FEATURE:
<221> NAME/KEY: misc_feature
<223> OTHER INFORMATION: ribulose 5-phosphate isomerase

<400> SEQUENCE: 4

Met Ala Ala Gly Val Pro Lys Ile Asp Ala Leu Glu Ser Leu Gly Asn
1               5                   10                  15

Pro Leu Glu Asp Ala Lys Arg Ala Ala Ala Tyr Arg Ala Val Asp Glu
            20                  25                  30

Asn Leu Lys Phe Asp Asp His Lys Ile Ile Gly Ile Gly Ser Gly Ser
        35                  40                  45

Thr Val Val Tyr Val Ala Glu Arg Ile Gly Gln Tyr Leu His Asp Pro
    50                  55                  60

Lys Phe Tyr Glu Val Ala Ser Lys Phe Ile Cys Ile Pro Thr Gly Phe
65                  70                  75                  80

Gln Ser Arg Asn Leu Ile Leu Asp Asn Lys Leu Gln Leu Gly Ser Ile
                85                  90                  95

Glu Gln Tyr Pro Arg Ile Asp Ile Ala Phe Asp Gly Ala Asp Glu Val
```

```
            100                 105                 110
Asp Glu Asn Leu Gln Leu Ile Lys Gly Gly Gly Ala Cys Leu Phe Gln
        115                 120                 125

Glu Lys Leu Val Ser Thr Ser Ala Lys Thr Phe Ile Val Val Ala Asp
    130                 135                 140

Ser Arg Lys Lys Ser Pro Lys His Leu Gly Lys Asn Trp Arg Gln Gly
145                 150                 155                 160

Val Pro Ile Glu Ile Val Pro Ser Ser Tyr Val Arg Val Lys Asn Asp
                165                 170                 175

Leu Leu Glu Gln Leu His Ala Glu Lys Val Asp Ile Arg Gln Gly Gly
            180                 185                 190

Ser Ala Lys Ala Gly Pro Val Val Thr Asp Asn Asn Asn Phe Ile Ile
        195                 200                 205

Asp Ala Asp Phe Gly Glu Ile Ser Asp Pro Arg Lys Leu His Arg Glu
    210                 215                 220

Ile Lys Leu Leu Val Gly Val Val Glu Thr Gly Leu Phe Ile Asp Asn
225                 230                 235                 240

Ala Ser Lys Ala Tyr Phe Gly Asn Ser Asp Gly Ser Val Glu Val Thr
                245                 250                 255

Glu Lys

<210> SEQ ID NO 5
<211> LENGTH: 238
<212> TYPE: PRT
<213> ORGANISM: Saccharomyces cerevisiae
<220> FEATURE:
<221> NAME/KEY: misc_feature
<223> OTHER INFORMATION: ribulose 5-phosphate epimerase

<400> SEQUENCE: 5

Met Val Lys Pro Ile Ile Ala Pro Ser Ile Leu Ala Ser Asp Phe Ala
1               5                   10                  15

Asn Leu Gly Cys Glu Cys His Lys Val Ile Asn Ala Gly Ala Asp Trp
            20                  25                  30

Leu His Ile Asp Val Met Asp Gly His Phe Val Pro Asn Ile Thr Leu
        35                  40                  45

Gly Gln Pro Ile Val Thr Ser Leu Arg Arg Ser Val Pro Arg Pro Gly
    50                  55                  60

Asp Ala Ser Asn Thr Glu Lys Lys Pro Thr Ala Phe Phe Asp Cys His
65                  70                  75                  80

Met Met Val Glu Asn Pro Glu Lys Trp Val Asp Asp Phe Ala Lys Cys
                85                  90                  95

Gly Ala Asp Gln Phe Thr Phe His Tyr Glu Ala Thr Gln Asp Pro Leu
            100                 105                 110

His Leu Val Lys Leu Ile Lys Ser Lys Gly Ile Lys Ala Ala Cys Ala
        115                 120                 125

Ile Lys Pro Gly Thr Ser Val Asp Val Leu Phe Glu Leu Ala Pro His
    130                 135                 140

Leu Asp Met Ala Leu Val Met Thr Val Glu Pro Gly Phe Gly Gly Gln
145                 150                 155                 160

Lys Phe Met Glu Asp Met Met Pro Lys Val Glu Thr Leu Arg Ala Lys
                165                 170                 175

Phe Pro His Leu Asn Ile Gln Val Asp Gly Gly Leu Gly Lys Glu Thr
            180                 185                 190

Ile Pro Lys Ala Ala Lys Ala Gly Ala Asn Val Ile Val Ala Gly Thr
```

```
            195                 200                 205
Ser Val Phe Thr Ala Ala Asp Pro His Asp Val Ile Ser Phe Met Lys
            210                 215                 220

Glu Glu Val Ser Lys Glu Leu Arg Ser Arg Asp Leu Leu Asp
225                 230                 235
```

<210> SEQ ID NO 6
<211> LENGTH: 680
<212> TYPE: PRT
<213> ORGANISM: Saccharomyces cerevisiae
<220> FEATURE:
<221> NAME/KEY: misc_feature
<223> OTHER INFORMATION: transketolase

<400> SEQUENCE: 6

```
Met Thr Gln Phe Thr Asp Ile Asp Lys Leu Ala Val Ser Thr Ile Arg
1               5                   10                  15

Ile Leu Ala Val Asp Thr Val Ser Lys Ala Asn Ser Gly His Pro Gly
            20                  25                  30

Ala Pro Leu Gly Met Ala Pro Ala His Val Leu Trp Ser Gln Met
        35                  40                  45

Arg Met Asn Pro Thr Asn Pro Asp Trp Ile Asn Arg Asp Arg Phe Val
50                  55                  60

Leu Ser Asn Gly His Ala Val Ala Leu Leu Tyr Ser Met Leu His Leu
65                  70                  75                  80

Thr Gly Tyr Asp Leu Ser Ile Glu Asp Leu Lys Gln Phe Arg Gln Leu
            85                  90                  95

Gly Ser Arg Thr Pro Gly His Pro Glu Phe Glu Leu Pro Gly Val Glu
            100                 105                 110

Val Thr Thr Gly Pro Leu Gly Gln Gly Ile Ser Asn Ala Val Gly Met
            115                 120                 125

Ala Met Ala Gln Ala Asn Leu Ala Ala Thr Tyr Asn Lys Pro Gly Phe
130                 135                 140

Thr Leu Ser Asp Asn Tyr Thr Tyr Val Phe Leu Gly Asp Gly Cys Leu
145                 150                 155                 160

Gln Glu Gly Ile Ser Ser Glu Ala Ser Ser Leu Ala Gly His Leu Lys
            165                 170                 175

Leu Gly Asn Leu Ile Ala Ile Tyr Asp Asp Asn Lys Ile Thr Ile Asp
            180                 185                 190

Gly Ala Thr Ser Ile Ser Phe Asp Glu Asp Val Ala Lys Arg Tyr Glu
            195                 200                 205

Ala Tyr Gly Trp Glu Val Leu Tyr Val Glu Asn Gly Asn Glu Asp Leu
            210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Thr Ile Gly Tyr Gly Ser Leu His
            245                 250                 255

Ala Gly Ser His Ser Val His Gly Ala Pro Leu Lys Ala Asp Asp Val
            260                 265                 270

Lys Gln Leu Lys Ser Lys Phe Gly Phe Asn Pro Asp Lys Ser Phe Val
            275                 280                 285

Val Pro Gln Glu Val Tyr Asp His Tyr Gln Lys Thr Ile Leu Lys Pro
            290                 295                 300

Gly Val Glu Ala Asn Asn Lys Trp Asn Lys Leu Phe Ser Glu Tyr Gln
305                 310                 315                 320
```

Lys Lys Phe Pro Glu Leu Gly Ala Glu Leu Ala Arg Arg Leu Ser Gly
            325                 330                 335

Gln Leu Pro Ala Asn Trp Glu Ser Lys Leu Pro Thr Tyr Thr Ala Lys
        340                 345                 350

Asp Ser Ala Val Ala Thr Arg Lys Leu Ser Glu Thr Val Leu Glu Asp
    355                 360                 365

Val Tyr Asn Gln Leu Pro Glu Leu Ile Gly Gly Ser Ala Asp Leu Thr
370                 375                 380

Pro Ser Asn Leu Thr Arg Trp Lys Glu Ala Leu Asp Phe Gln Pro Pro
385                 390                 395                 400

Ser Ser Gly Ser Gly Asn Tyr Ser Gly Arg Tyr Ile Arg Tyr Gly Ile
                405                 410                 415

Arg Glu His Ala Met Gly Ala Ile Met Asn Gly Ile Ser Ala Phe Gly
            420                 425                 430

Ala Asn Tyr Lys Pro Tyr Gly Gly Thr Phe Leu Asn Phe Val Ser Tyr
        435                 440                 445

Ala Ala Gly Ala Val Arg Leu Ser Ala Leu Ser Gly His Pro Val Ile
    450                 455                 460

Trp Val Ala Thr His Asp Ser Ile Gly Val Gly Glu Asp Gly Pro Thr
465                 470                 475                 480

His Gln Pro Ile Glu Thr Leu Ala His Phe Arg Ser Leu Pro Asn Ile
                485                 490                 495

Gln Val Trp Arg Pro Ala Asp Gly Asn Glu Val Ser Ala Ala Tyr Lys
            500                 505                 510

Asn Ser Leu Glu Ser Lys His Thr Pro Ser Ile Ile Ala Leu Ser Arg
        515                 520                 525

Gln Asn Leu Pro Gln Leu Glu Gly Ser Ser Ile Glu Ser Ala Ser Lys
    530                 535                 540

Gly Gly Tyr Val Leu Gln Asp Val Ala Asn Pro Asp Ile Ile Leu Val
545                 550                 555                 560

Ala Thr Gly Ser Glu Val Ser Leu Ser Val Glu Ala Ala Lys Thr Leu
                565                 570                 575

Ala Ala Lys Asn Ile Lys Ala Arg Val Val Ser Leu Pro Asp Phe Phe
            580                 585                 590

Thr Phe Asp Lys Gln Pro Leu Glu Tyr Arg Leu Ser Val Leu Pro Asp
        595                 600                 605

Asn Val Pro Ile Met Ser Val Glu Val Leu Ala Thr Thr Cys Trp Gly
    610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
                645                 650                 655

Ala Glu Arg Ala Gln Lys Thr Ile Ala Phe Tyr Lys Gly Asp Lys Leu
            660                 665                 670

Ile Ser Pro Leu Lys Lys Ala Phe
        675                 680

<210> SEQ ID NO 7
<211> LENGTH: 335
<212> TYPE: PRT
<213> ORGANISM: Saccharomyces cerevisiae
<220> FEATURE:
<221> NAME/KEY: misc_feature
<223> OTHER INFORMATION: transaldolase

<400> SEQUENCE: 7

Met Ser Glu Pro Ala Gln Lys Gln Lys Val Ala Asn Asn Ser Leu
1               5                   10                  15

Glu Gln Leu Lys Ala Ser Gly Thr Val Val Ala Asp Thr Gly Asp
            20                  25                  30

Phe Gly Ser Ile Ala Lys Phe Gln Pro Gln Asp Ser Thr Thr Asn Pro
        35                  40                  45

Ser Leu Ile Leu Ala Ala Lys Gln Pro Thr Tyr Ala Lys Leu Ile
50                  55                  60

Asp Val Ala Val Glu Tyr Gly Lys Lys His Gly Lys Thr Thr Glu Glu
65                  70                  75                  80

Gln Val Glu Asn Ala Val Asp Arg Leu Leu Val Glu Phe Gly Lys Glu
            85                  90                  95

Ile Leu Lys Ile Val Pro Gly Arg Val Ser Thr Glu Val Asp Ala Arg
                100                 105                 110

Leu Ser Phe Asp Thr Gln Ala Thr Ile Glu Lys Ala Arg His Ile Ile
            115                 120                 125

Lys Leu Phe Glu Gln Glu Gly Val Ser Lys Glu Arg Val Leu Ile Lys
        130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
                165                 170                 175

Ala Val Ala Cys Ala Glu Ala Gln Val Thr Leu Ile Ser Pro Phe Val
            180                 185                 190

Gly Arg Ile Leu Asp Trp Tyr Lys Ser Ser Thr Gly Lys Asp Tyr Lys
        195                 200                 205

Gly Glu Ala Asp Pro Gly Val Ile Ser Val Lys Lys Ile Tyr Asn Tyr
    210                 215                 220

Tyr Lys Lys Tyr Gly Tyr Lys Thr Ile Val Met Gly Ala Ser Phe Arg
225                 230                 235                 240

Ser Thr Asp Glu Ile Lys Asn Leu Ala Gly Val Asp Tyr Leu Thr Ile
                245                 250                 255

Ser Pro Ala Leu Leu Asp Lys Leu Met Asn Ser Thr Glu Pro Phe Pro
            260                 265                 270

Arg Val Leu Asp Pro Val Ser Ala Lys Lys Glu Ala Gly Asp Lys Ile
        275                 280                 285

Ser Tyr Ile Ser Asp Glu Ser Lys Phe Arg Phe Asp Leu Asn Glu Asp
    290                 295                 300

Ala Met Ala Thr Glu Lys Leu Ser Glu Gly Ile Arg Lys Phe Ser Ala
305                 310                 315                 320

Asp Ile Val Thr Leu Phe Asp Leu Ile Glu Lys Lys Val Thr Ala
                325                 330                 335

<210> SEQ ID NO 8
<211> LENGTH: 327
<212> TYPE: PRT
<213> ORGANISM: Saccharomyces cerevisiae
<220> FEATURE:
<221> NAME/KEY: misc_feature
<223> OTHER INFORMATION: aldose reductase

<400> SEQUENCE: 8

Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile

```
                   20                  25                  30

Tyr Glu Ala Ile Lys Leu Gly Tyr Arg Leu Phe Asp Gly Ala Cys Asp
            35                  40                  45

Tyr Gly Asn Glu Lys Glu Val Gly Glu Gly Ile Arg Lys Ala Ile Ser
        50                  55                  60

Glu Gly Leu Val Ser Arg Lys Asp Ile Phe Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
    210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 9
<211> LENGTH: 1669
<212> TYPE: DNA
<213> ORGANISM: Piromyces sp.
<220> FEATURE:
<221> NAME/KEY: misc_feature
<223> OTHER INFORMATION: xylose isomerase

<400> SEQUENCE: 9
gtaaatggct aaggaatatt tcccacaaat tcaaaagatt aagttcgaag gtaaggattc      60
taagaatcca ttagccttcc actactacga tgctgaaaag gaagtcatgg gtaagaaaat     120
gaaggattgg ttacgtttcg ccatggcctg gtggcacact ctttgcgccg aaggtgctga    180
ccaattcggt ggaggtacaa agtctttccc atggaacgaa ggtactgatg ctattgaaat    240
tgccaagcaa aaggttgatg ctggtttcga aatcatgcaa aagcttggta ttccatacta    300
```

```
ctgtttccac gatgttgatc ttgtttccga aggtaactct attgaagaat acgaatccaa    360
ccttaaggct gtcgttgctt acctcaagga aaagcaaaag gaaaccggta ttaagcttct    420
ctggagtact gctaacgtct tcggtcacaa gcgttacatg aacggtgcct ccactaaccc    480
agactttgat gttgtcgccc gtgctattgt tcaaattaag aacgccatag acgccggtat    540
tgaacttggt gctgaaaact acgtcttctg gggtggtcgt gaaggttaca tgagtctcct    600
taacactgac caaaagcgtg aaaaggaaca catggccact atgcttacca tggctcgtga    660
ctacgctcgt tccaagggat tcaagggtac tttcctcatt gaaccaaagc caatggaacc    720
aaccaagcac caatacgatg ttgacactga accgctatt ggtttcctta aggcccacaa     780
cttagacaag gacttcaagg tcaacattga agttaaccac gctactcttg ctggtcacac    840
tttcgaacac gaacttgcct gtgctgttga tgctggtatg ctcggttcca ttgatgctaa    900
ccgtggtgac taccaaaacg gttgggatac tgatcaattc ccaattgatc aatacgaact    960
cgtccaagct tggatggaaa tcatccgtgg tggtggtttc gttactggtg gtaccaactt   1020
cgatgccaag actcgtcgta actctactga cctcgaagac atcatcattg cccacgtttc   1080
tggtatggat gctatggctc gtgctcttga aaacgctgcc aagctcctcc aagaatctcc   1140
atacaccaag atgaagaagg aacgttacgc ttccttcgac agtggtattg gtaaggactt   1200
tgaagatggt aagctcaccc tcgaacaagt ttacgaatac ggtaagaaga acggtgaacc   1260 aaagcaaaact tctggtaagc aagaactcta cgaagctatt gttgccatgt accaataagt   1320
taatcgtagt taaattggta aaataattgt aaaatcaata aacttgtcaa tcctccaatc   1380
aagtttaaaa gatcctatct ctgtactaat taaatatagt acaaaaaaaa atgtataaac   1440
aaaaaaaagt ctaaaagacg gaagaattta atttagggaa aaaataaaaa taataataaa   1500
caatagataa atcctttata ttaggaaaat gtcccattgt attattttca tttctactaa   1560
aaaagaaagt aaataaaaca caagaggaaa ttttccctt tttttttttt tgtaataaat    1620
tttatgcaaa tataaatata aataaaataa taaaaaaaaa aaaaaaaa                1669
```

<210> SEQ ID NO 10
<211> LENGTH: 1317
<212> TYPE: DNA
<213> ORGANISM: Bacteroides thetaiotaomicron
<220> FEATURE:
<221> NAME/KEY: misc_feature
<223> OTHER INFORMATION: xylose isomerase

<400> SEQUENCE: 10

```
atggcaacaa agaatttttt tccgggaatt gaaaagatta aatttgaagg taaagatagt     60
aagaacccga tggcattccg ttattacgat gcagagaagg tgattaatgg taaaaagatg    120
aaggattggc tgagattcgc tatggcatgg tggcacacat tgtgcgctga aggtggtgat    180
cagttcggtg gcggaacaaa gcaattccca tggaatggta atgcagatgc tatacaggca    240
gcaaaagata agatggatgc aggatttgaa ttcatgcaga gatgggtat cgaatactat     300 tgcttccatg acgtagactt ggtttcggaa ggtgccagtg tagaagaata cgaagctaac    360
ctgaaagaaa tcgtagctta tgcaaaacag aaacaggcag aaaccggtat caaactactg    420
tggggtactg ctaatgtatt cggtcacgcc cgctatatga acggtgcagc taccaatcct    480
gacttcgatg tagtagctcg tgctgctgtt cagatcaaaa atgcgattga tgcaacgatt    540
gaacttggcg gagagaatta tgtgttttgg ggtggtcgtg aaggctatat gtctcttctg    600
aacacagatc agaaacgtga aaaagaacac cttgcacaga tgttgacgat tgctcgtgac    660
```

```
tatgcccgtg cccgtggttt caaaggtact ttcctgatcg aaccgaaacc gatggaaccg    720
actaaacatc aatatgacgt agatacggaa actgtaatcg gcttcctgaa agctcatggt    780
ctggataagg atttcaaagt aaatatcgag gtgaatcacg caactttggc aggtcacact    840
ttcgagcatg aattggctgt agctgtagac aatggtatgt tgggctcaat tgacgccaat    900
cgtggtgact atcagaatgg ctgggataca gaccaattcc cgatcgacaa ttatgaactg    960
actcaggcta tgatgcagat tatccgtaat ggtggtctcg gtaccggtgg tacgaacttt   1020
gatgctaaaa cccgtcgtaa ttctactgat ctggaagata tctttattgc tcacatcgca   1080
ggtatggacg ctatggcccg tgcactcgaa agtgcagcgg ctctgctcga cgaatctccc   1140
tataagaaga tgctggctga ccgttatgct tcatttgatg ggggcaaagg taagaatttt   1200
gaagacggca agctgactct ggaggatgtg gttgcttatg caaaaacaaa aggcgaaccg   1260
aaacagacta gcggcaagca agaactttat gaggcaattc tgaatatgta ttgctaa      1317

<210> SEQ ID NO 11
<211> LENGTH: 2467
<212> TYPE: DNA
<213> ORGANISM: Saccharomyces cerevisiae
<220> FEATURE:
<221> NAME/KEY: misc_feature
<223> OTHER INFORMATION: xylulokinase

<400> SEQUENCE: 11
ggatccaaga ccattattcc atcagaatgg aaaaaagttt aaaagatcac ggagattttg     60
ttcttctgag cttctgctgt ccttgaaaac aaattattcc gctggccgcc ccaaacaaaa    120
acaaccccga tttaataaca ttgtcacagt attagaaatt ttcttttttac aaattaccat    180 ttccagctta ctacttccta taatcctcaa tcttcagcaa gcgacgcagg gaatagccgc    240
tgaggtgcat aactgtcact tttcaattcg gccaatgcaa tctcaggcgg acgaataagg    300
gggccctctc gagaaaaaca aaaggaggat gagattagta cttttaatgtt gtgttcagta    360 attcagagac agacaagaga ggtttccaac acaatgtctt tagactcata ctatcttggg    420
tttgatcttt cgacccaaca actgaaatgt ctcgccatta accaggacct aaaaattgtc    480
cattcagaaa cagtggaatt tgaaaaggat cttccgcatt atcacacaaa gaagggtgtc    540
tatatacacg gcgacactat cgaatgtccc gtagccatgt ggttaggggc tctagatctg    600
gttctctcga aatatcgcga ggctaaattt ccattgaaca aagttatggc cgtctcaggg    660
tcctgccagc agcacgggtc tgtctactgg tcctcccaag ccgaatctct gttagagcaa    720
ttgaataaga aaccggaaaa agatttattg cactacgtga gctctgtagc atttgcaagg    780
caaaccgccc ccaattggca agaccacagt actgcaaagc aatgtcaaga gtttgaagag    840
tgcataggtg ggcctgaaaa aatggctcaa ttaacagggt ccagagccca ttttagattt    900
actggtcctc aaattctgaa aattgcacaa ttagaaccag aagcttacga aaaaacaaag    960
accatttctt tagtgtctaa tttttgact tctatcttag tgggccatct tgttgaatta   1020
gaggaggcag atgcctgtgg tatgaacctt tatgatatac gtgaaagaaa attcatgtat   1080
gagctactac atctaattga tagttcttct aaggataaaa ctatcagaca aaattaatg    1140 agagcaccca tgaaaaattt gatagcgggt accatctgta aatattttat tgagaagtac   1200
ggtttcaata caaactgcaa ggtctctccc atgactgggg ataatttagc cactatatgt   1260
tctttacccc tgcggaagaa tgacgttctc gtttccctag aacaagtac tacagttctt   1320 ctggtcaccg ataagtatca cccctctccg aactatcatc ttttcattca tccaactctg   1380
```

```
ccaaaccatt atatgggtat gatttgttat tgtaatggtt ctttggcaag ggagaggata    1440
agagacgagt taaacaaaga acgggaaaat aattatgaga agactaacga ttggactctt    1500
tttaatcaag ctgtgctaga tgactcagaa agtagtgaaa atgaattagg tgtatatttt    1560
cctctggggg agatcgttcc tagcgtaaaa gccataaaca aaagggttat cttcaatcca    1620
aaaacgggta tgattgaaag agaggtggcc aagttcaaag acaagaggca cgatgccaaa    1680
aatattgtag aatcacaggc tttaagttgc agggtaagaa tatctcccct gctttcggat    1740
tcaaacgcaa gctcacaaca gagactgaac gaagatacaa tcgtgaagtt tgattacgat    1800
gaatctccgc tgcgggacta cctaaataaa aggccagaaa ggactttttt tgtaggtggg    1860
gcttctaaaa acgatgctat tgtgaagaag tttgctcaag tcattggtgc tacaaagggt    1920
aattttaggc tagaaacacc aaactcatgt gcccttggtg gttgttataa ggccatgtgg    1980
tcattgttat atgactctaa taaaattgca gttccttttg ataaatttct gaatgacaat    2040
tttccatggc atgtaatgga aagcatatcc gatgtggata tgaaaattg gatcgctata    2100 attccaagat tgtcccctta agcgaactgg aaaagactct catctaaaat atgtttgaat    2160
aatttatcat gccctgacaa gtacacacaa acacagacac ataatataca tacatatata    2220
tatatcaccg ttattatgcg tgcacatgac aatgcccttg tatgtttcgt atactgtagc    2280
aagtagtcat cattttgttc cccgttcgga aaatgacaaa aagtaaaatc aataaatgaa    2340
gagtaaaaaa caatttatga aagggtgagc gaccagcaac gagagagaca aatcaaatta    2400
gcgctttcca gtgagaatat aagagagcat tgaaagagct aggttattgt taaatcatct    2460
cgagctc                                                              2467
```

<210> SEQ ID NO 12
<211> LENGTH: 777
<212> TYPE: DNA
<213> ORGANISM: Saccharomyces cerevisiae
<220> FEATURE:
<221> NAME/KEY: misc_feature
<223> OTHER INFORMATION: ribulose 5-phosphate isomerase

<400> SEQUENCE: 12

```
atggctgccg gtgtcccaaa aattgatgcg ttagaatctt tgggcaatcc tttggaggat      60
gccaagagag ctgcagcata cagagcagtt gatgaaaatt taaaatttga tgatcacaaa     120
attattggaa ttggtagtgg tagcacagtg gtttatgttg ccgaaagaat tggacaatat     180
ttgcatgacc ctaaatttta tgaagtagcg tctaaattca tttgcattcc aacaggattc     240
caatcaagaa acttgatttt ggataacaag ttgcaattag gctccattga acagtatcct     300
cgcattgata tagcgtttga cggtgctgat gaagtggatg agaatttaca attaattaaa     360
ggtggtggtg cttgtctatt tcaagaaaaa ttggttagta ctagtgctaa aaccttcatt     420
gtcgttgctg attcaagaaa aaagtcacca aacatttag gtaagaactg gaggcaaggt     480
gttcccattg aaattgtacc ttcctcatac gtgagggtca agaatgatct attagaacaa     540
ttgcatgctg aaaaagttga catcagacaa ggaggttctg ctaaagcagg tcctgttgta     600
actgacaata taacttcat tatcgatgcg gatttcggtg aaatttccga tccaagaaaa     660
ttgcatagag aaatcaaact gttagtgggc gtggtggaaa caggtttatt catcgacaac     720
gcttcaaaag cctacttcgg taattctgac ggtagtgttg aagttaccga aaagtga        777
```

<210> SEQ ID NO 13
<211> LENGTH: 1328

<212> TYPE: DNA
<213> ORGANISM: Saccharomyces cerevisiae
<220> FEATURE:
<221> NAME/KEY: misc_feature
<223> OTHER INFORMATION: ribulose 5-phosphate epimerase

<400> SEQUENCE: 13

```
gttaggcact tacgtatctt gtatagtagg aatggctcgg tttatgtata ttaggagatc      60
aaaacgagaa aaaatacca tatcgtatag tatagagagt ataaatataa gaaatgccgc     120
atatgtacaa ctaatctagc aaatctctag aacgcaattc cttcgagact tcttctttca     180
tgaaggagat aacatcgtgc gggtcagctg cagtgaaaac actggtacca gcgacaataa     240
cgttggcacc ggctttggcg gctttcggga tggtctcctt gcccaaacca ccatcgactt     300
ggatattcaa atgggggaac ttggctctca aagtttccac ttttggcatc atgtcttcca     360
tgaattttg gcctccaaac ccaggttcca cagtcataac aagagccata tccaaatgag     420
gagctagttc aaataaaacg tcaacagaag taccaggttt gatggcgcat gcagctttga     480
tgcccttaga cttaatcaac ttaactaaat gcaaagggtc ttgtgtggcc tcgtagtgga     540
acgtaaattg gtcagcacca catttagcaa aatcgtcgac ccattttttca ggattttcaa     600
ccatcatgtg acaatcgaag aacgcagtgg gcttcttttc tgtgttgcta gcatcgccag     660
ggcgtggcac agaacgacgt agggaggtaa caattggttg gcccagagta atgtttggaa     720
caaaatggcc gtccatgaca tcgatatgta accaatctgc gccggcgttg atgaccttat     780
gacattcgca acccaagttg gcgaagtcag aagcaaggat actgggagct ataattggtt     840
tgaccatttt ttcttgtgtg tttacctcgc tcttggaatt agcaaatggc cttcttgcat     900
gaaattgtat cgagtttgct ttattttct ttttacgggc ggattctttc tattctggct     960
ttcctataac agagatcatg aaagaagttc cagcttacgg atcaagaaag tacctataca    1020
tatacaaaaa tctgattact ttcccagctc gacttggata gctgttcttg ttttctcttg    1080
gcgacacatt ttttgtttct gaagccacgt cctgctttat aagaggacat ttaaagttgc    1140
aggacttgaa tgcaattacc ggaagaagca accaaccggc atggttcagc atacaataca    1200
catttgatta gaaaagcaga gaataaatag acatgatacc tctctttta tcctctgcag    1260
cgtattattg tttattccac gcaggcatcg gtcgttggct gttgttatgt ctcagataag    1320
cgcgtttg                                                              1328
```

<210> SEQ ID NO 14
<211> LENGTH: 2046
<212> TYPE: DNA
<213> ORGANISM: Saccharomyces cerevisiae
<220> FEATURE:
<221> NAME/KEY: misc_feature
<223> OTHER INFORMATION: transketolase

<400> SEQUENCE: 14

```
atggcacagt tctccgacat tgataaactt gcggtttcca ctttaagatt actttccgtt     60
gaccaggtgg aaagcgcaca atctggccac ccaggtgcac actaggatt ggcaccagtt    120
gcccatgtaa ttttcaagca actgcgctgt aaccctaaca atgaacattg gatcaataga    180
gacaggttg ttctgtcgaa cggtcactca tgcgctcttc tgtactcaat gctccatcta    240
ttaggatacg attactctat cgaggacttg agacaattta gacaagtaaa ctcaaggaca    300
ccgggtcatc cagaattcca ctcagcggga gtggaaatca cttccggtcc gctaggccag    360
ggtatctcaa atgctgttgg tatggcaata gcgcaggcca actttgccgc cacttataac    420
```

-continued

```
gaggatggct ttcccatttc cgactcatat acgtttgcta ttgtagggga tggttgctta    480
caagagggtg tttcttcgga gacctcttcc ttagcgggac atctgcaatt gggtaacttg    540
attacgtttt atgacagtaa tagcatttcc attgacggta aaacctcgta ctcgttcgac    600
gaagatgttt tgaagcgata cgaggcatat ggttgggaag tcatggaagt cgataaagga    660
gacgacgata tggaatccat ttctagcgct ttggaaaagg caaaactatc gaaggacaag    720
ccaaccataa tcaaggtaac tactacaatt ggatttgggt ccctacaaca gggtactgct    780
ggtgttcatg ggtccgcttt gaaggcagat gatgttaaac agttgaagaa gaggtggggg    840
tttgacccaa ataaatcatt tgtagtacct caagaggtgt acgattatta taagaagact    900
gttgtggaac ccggtcaaaa acttaatgag gaatgggata ggatgtttga agaatacaaa    960
accaaatttc ccgagaaggg taagaattg caaagaagat tgaatggtga gttaccggaa    1020 ggtgggaaa agcatttacc gaagtttact ccggacgacg atgctctggc aacaagaaag    1080
acatcccagc aggtgctgac gaacatggtc aagttttgc ctgaattgat cggtggttct    1140
gccgatttga caccttcgaa tctgacaagg tgggaaggcg cggtagattt ccaacctccc    1200 attcccaac taggtaacta tgcaggaagg tacattagat acggtgtgag ggaacacgga    1260
atgggtgcca ttatgaacgg tatctctgcc tttggtgcaa actacaagcc ttacggtggt    1320
acctttttga acttcgtctc ttatgctgca ggagccgtta ggttagccgc cttgtctggt    1380
aatccagtca tttgggttgc aacacatgac tctatcgggc ttggtgagga tggtccaacg    1440
caccaaccta ttgaaactct ggctcacttg agggctattc caaacatgca tgtatggaga    1500
cctgctgatg gtaacgaaac ttctgctgcg tattattctg ctatcaaatc tggtcgaaca    1560
ccatctgttg tggctttatc acgacagaat cttcctcaat tggagcattc ctcttttgaa    1620
aaagccttga agggtggcta tgtgatccat gacgtggaga atcctgatat tatcctggtg    1680
tcaacaggat cagaagtctc catttctata gatgcagcca aaaattgta cgatactaaa    1740 aaaatcaaag caagagttgt ttccctgcca gactttttata cttttgacag gcaaagtgaa    1800
gaatacagat tctctgttct accagacggt gttccgatca tgtcctttga agtattggct    1860
acttcaagct ggggtaagta tgctcatcaa tcgttcggac tcgacgaatt tggtcgttca    1920
ggcaaggggc ctgaaattta caaattgttc gatttcacag cggacggtgt tgcgtcaagg    1980
gctgaaaaga caatcaatta ctacaaagga aagcagttgc tttctcctat gggaagagct    2040
ttctaa                                                              2046
```

```
<210> SEQ ID NO 15
<211> LENGTH: 1008
<212> TYPE: DNA
<213> ORGANISM: Saccharomyces cerevisiae
<220> FEATURE:
<221> NAME/KEY: misc_feature
<223> OTHER INFORMATION: transaldolase

<400> SEQUENCE: 15
atgtctgaac cagctcaaaa gaaacaaaag gttgctaaca actctctaga acaattgaaa     60
gcctccggca ctgtcgttgt tgccgacact ggtgatttcg gctctattgc caagtttcaa    120
cctcaagact ccacaactaa cccatcattg atcttggctg ctgccaagca accaacttac    180
gccaagttga tcgatgttgc cgtggaatac ggtaagaagc atggtaagac caccgaagaa    240
caagtcgaaa atgctgtgga cagattgtta gtcgaattcg gtaaggagat cttaaagatt    300
gttccaggca gagtctccac cgaagttgat gctagattgt cttttgacac tcaagctacc    360
```

```
attgaaaagg ctagacatat cattaaattg tttgaacaag aaggtgtctc caaggaaaga    420
gtccttatta aaattgcttc cacttgggaa ggtattcaag ctgccaaaga attggaagaa    480
aaggacggta tccactgtaa tttgactcta ttattctcct tcgttcaagc agttgcctgt    540
gccgaggccc aagttacttt gatttcccca tttgttggta gaattctaga ctggtacaaa    600
tccagcactg gtaaagatta caagggtgaa gccgacccag gtgttatttc cgtcaagaaa    660
atctacaact actacaagaa gtacggttac aagactattg ttatgggtgc ttcttttcaga   720 agcactgacg aaatcaaaaa cttggctggt gttgactatc taacaatttc tccagcttta    780
ttggacaagt tgatgaacag tactgaacct ttcccaagag ttttggaccc tgtctccgct    840
aagaaggaag ccggcgacaa gatttcttac atcagcgacg aatctaaatt cagattcgac    900
ttgaatgaag acgctatggc cactgaaaaa ttgtccgaag gtatcagaaa attctctgcc    960
gatattgtta ctctattcga cttgattgaa aagaaagtta ccgcttaa              1008
```

<210> SEQ ID NO 16
<211> LENGTH: 984
<212> TYPE: DNA
<213> ORGANISM: Saccharomyces cerevisiae
<220> FEATURE:
<221> NAME/KEY: misc_feature
<223> OTHER INFORMATION: aldose reductase

<400> SEQUENCE: 16

```
atgtcttcac tggttactct taataacggt ctgaaaatgc ccctagtcgg cttagggtgc     60
tggaaaattg acaaaaaagt ctgtgcgaat caaatttatg aagctatcaa attaggctac    120
cgtttattcg atggtgcttg cgactacggc aacgaaaagg aagttggtga aggtatcagg    180
aaagccatct ccgaaggtct tgtttctaga aaggatatat ttgttgtttc aaagttatgg    240
aacaattttc accatcctga tcatgtaaaa ttagctttaa agaagacctt aagcgatatg    300
ggacttgatt atttagacct gtattatatt cacttcccaa tcgccttcaa atatgttcca    360
tttgaagaga ataccctcc aggattctat acgggcgcag atgacgagaa gaaaggtcac    420
atcaccgaag cacatgtacc aatcatagat acgtaccggg ctctggaaga atgtgttgat    480
gaaggcttga ttaagtctat tggtgttttcc aactttcagg gaagcttgat tcaagattta    540
ttacgtggtt gtagaatcaa gcccgtggct ttgcaaattg aacaccatcc ttatttgact    600
caagaacacc tagttgagtt ttgtaaatta acgatatcc aagtagttgc ttactcctcc    660
ttcggtcctc aatcattcat tgagatggac ttacagttgg caaaaaccac gccaactctg    720
ttcgagaatg atgtaatcaa gaaggtctca caaaaccatc caggcagtac cacttcccaa    780
gtattgctta gatgggcaac tcagagaggc attgccgtca ttccaaaatc ttccaagaag    840
gaaaggttac ttggcaacct agaaatcgaa aaaaagttca ctttaacgga gcaagaattg    900 aaggatatttt ctgcactaaa tgccaacatc agatttaatg atccatggac ctggttggat    960
ggtaaattcc ccacttttgc ctga                                           984
```

<210> SEQ ID NO 17
<211> LENGTH: 494
<212> TYPE: PRT
<213> ORGANISM: Piromyces sp.
<220> FEATURE:
<221> NAME/KEY: misc_feature
<223> OTHER INFORMATION: xylulose kinase

<400> SEQUENCE: 17

Met Lys Thr Val Ala Gly Ile Asp Leu Gly Thr Gln Ser Met Lys Val

```
1               5                   10                  15
Val Ile Tyr Asp Tyr Glu Lys Lys Glu Ile Glu Ser Ala Ser Cys
            20                  25                  30

Pro Met Glu Leu Ile Ser Glu Ser Asp Gly Thr Arg Glu Gln Thr Thr
            35                  40                  45

Glu Trp Phe Asp Lys Gly Leu Glu Val Cys Phe Gly Lys Leu Ser Ala
50                  55                  60

Asp Asn Lys Lys Thr Ile Glu Ala Ile Gly Ile Ser Gly Gln Leu His
65                  70                  75                  80

Gly Phe Val Pro Leu Asp Ala Asn Gly Lys Ala Leu Tyr Asn Ile Lys
                85                  90                  95

Leu Trp Cys Asp Thr Ala Thr Val Glu Glu Cys Lys Ile Ile Thr Asp
                100                 105                 110

Ala Ala Gly Gly Asp Lys Ala Val Ile Asp Ala Leu Gly Asn Leu Met
                115                 120                 125

Leu Thr Gly Phe Thr Ala Pro Lys Ile Leu Trp Leu Lys Arg Asn Lys
130                 135                 140

Pro Glu Ala Phe Ala Asn Leu Lys Tyr Ile Met Leu Pro His Asp Tyr
145                 150                 155                 160

Leu Asn Trp Lys Leu Thr Gly Asp Tyr Val Met Glu Tyr Gly Asp Ala
                165                 170                 175

Ser Gly Thr Ala Leu Phe Asp Ser Lys Asn Arg Cys Trp Ser Lys Lys
                180                 185                 190

Ile Cys Asp Ile Ile Asp Pro Lys Leu Leu Asp Leu Leu Pro Lys Leu
                195                 200                 205

Ile Glu Pro Ser Ala Pro Ala Gly Lys Val Asn Asp Glu Ala Ala Lys
210                 215                 220

Ala Tyr Gly Ile Pro Ala Gly Ile Pro Val Ser Ala Gly Gly Asp
225                 230                 235                 240

Asn Met Met Gly Ala Val Gly Thr Gly Thr Val Ala Asp Gly Phe Leu
                245                 250                 255

Thr Met Ser Met Gly Thr Ser Gly Thr Leu Tyr Gly Tyr Ser Asp Lys
                260                 265                 270

Pro Ile Ser Asp Pro Ala Asn Gly Leu Ser Gly Phe Cys Ser Ser Thr
                275                 280                 285

Gly Gly Trp Leu Pro Leu Leu Cys Thr Met Asn Cys Thr Val Ala Thr
                290                 295                 300

Glu Phe Val Arg Asn Leu Phe Gln Met Asp Ile Lys Glu Leu Asn Val
305                 310                 315                 320

Glu Ala Ala Lys Ser Pro Cys Gly Ser Glu Gly Val Leu Val Ile Pro
                325                 330                 335

Phe Phe Asn Gly Glu Arg Thr Pro Asn Leu Pro Asn Gly Arg Ala Ser
                340                 345                 350

Ile Thr Gly Leu Thr Ser Ala Asn Thr Ser Arg Ala Asn Ile Ala Arg
                355                 360                 365

Ala Ser Phe Glu Ser Ala Val Phe Ala Met Arg Gly Gly Leu Asp Ala
                370                 375                 380

Phe Arg Lys Leu Gly Phe Gln Pro Lys Glu Ile Arg Leu Ile Gly Gly
385                 390                 395                 400

Gly Ser Lys Ser Asp Leu Trp Arg Gln Ile Ala Ala Asp Ile Met Asn
                405                 410                 415

Leu Pro Ile Arg Val Pro Leu Leu Glu Glu Ala Ala Leu Gly Gly
                420                 425                 430
```

```
Ala Val Gln Ala Leu Trp Cys Leu Lys Asn Gln Ser Gly Lys Cys Asp
        435                 440                 445

Ile Val Glu Leu Cys Lys Glu His Ile Lys Ile Asp Glu Ser Lys Asn
    450                 455                 460

Ala Asn Pro Ile Ala Glu Asn Val Ala Val Tyr Asp Lys Ala Tyr Asp
465                 470                 475                 480

Glu Tyr Cys Lys Val Val Asn Thr Leu Ser Pro Leu Tyr Ala
                485                 490

<210> SEQ ID NO 18
<211> LENGTH: 2041
<212> TYPE: DNA
<213> ORGANISM: Piromyces sp.
<220> FEATURE:
<221> NAME/KEY: misc_feature
<223> OTHER INFORMATION: xylulose kinase

<400> SEQUENCE: 18
```

| | | | | | |
|---|---|---|---|---|---|
| attatataaa | ataactttaa | ataaaacaat | ttttatttgt | ttatttaatt | attcaaaaaa    60 |
| aattaaagta | aaagaaaaat | aatacagtag | aacaatagta | ataatatcaa | aatgaagact   120 |
| gttgctggta | ttgatcttgg | aactcaaagt | atgaaagtcg | ttatttacga | ctatgaaaag   180 |
| aaagaaatta | ttgaaagtgc | tagctgtcca | atggaattga | tttccgaaag | tgacggtacc   240 |
| cgtgaacaaa | ccactgaatg | gtttgacaag | ggtcttgaag | tttgttttgg | taagcttagt   300 |
| gctgataaca | aaaagactat | tgaagctatt | ggtatttctg | gtcaattaca | cggttttgtt   360 |
| cctcttgatg | ctaacggtaa | ggctttatac | aacatcaaac | tttggtgtga | tactgctacc   420 |
| gttgaagaat | gtaagattat | cactgatgct | gccggtggtg | acaaggctgt | tattgatgcc   480 |
| cttggtaacc | ttatgctcac | cggtttcacc | gctccaaaga | tcctctggct | caagcgcaac   540 |
| aagccagaag | ctttcgctaa | cttaaagtac | attatgcttc | cacacgatta | cttaaactgg   600 |
| aagcttactg | gtgattacgt | tatggaatac | ggtgatgcct | ctggtaccgc | tctcttcgat   660 |
| tctaagaacc | gttgctggtc | taagaagatt | tgcgatatca | ttgacccaaa | acttttagat   720 |
| ttacttccaa | agttaattga | accaagcgct | ccagctggta | aggttaatga | tgaagccgct   780 |
| aaggcttacg | gtattccagc | cggtattcca | gtttccgctg | gtggtggtga | taacatgatg   840 |
| ggtgctgttg | gtactggtac | tgttgctgat | ggtttcctta | ccatgtctat | gggtacttct   900 |
| ggtactcttt | acggttacag | tgacaagcca | attagtgacc | cagctaatgg | tttaagtggt   960 |
| ttctgttctt | ctactggtgg | atggcttcca | ttactttgta | ctatgaactg | tactgttgcc  1020 |
| actgaattcg | ttcgtaacct | cttccaaatg | gatattaagg | aacttaatgt | tgaagctgcc  1080 |
| aagtctccat | gtggtagtga | aggtgtttta | gttattccat | tcttcaatgg | tgaaagaact  1140 |
| ccaaacttac | caaacggtcg | tgctagtatt | actggtctta | cttctgctaa | caccagccgt  1200 |
| gctaacattg | ctcgtgctag | tttcgaatcc | gccgttttcg | ctatgcgtgg | tggtttagat  1260 |
| gctttccgta | agttaggttt | ccaaccaaag | gaaattcgtc | ttattggtgg | tggttctaag  1320 |
| tctgatctct | ggagacaaat | tgccgctgat | atcatgaacc | ttccaatcag | agttccactt  1380 |
| ttagaagaag | ctgctgctct | tggtggtgct | gttcaagctt | atggtgtctc | taagaaccaa  1440 |
| tctggtaagt | gtgatattgt | tgaactttgc | aaagaacaca | ttaagattga | tgaatctaag  1500 |
| aatgctaacc | caattgccga | aaatgttgct | gtttacgaca | aggcttacga | tgaatactgc  1560 |
| aaggttgtaa | atactctttc | tccattatat | gcttaaattg | ccaatgtaaa | aaaaaatata  1620 |
| atgccatata | attgccttgt | caatacactg | ttcatgttca | tataatcata | ggacattgaa  1680 |

```
tttacaaggt ttatacaatt aatatctatt atcatattat tatacagcat ttcattttct    1740
aagattagac gaaacaattc ttggttcctt gcaatataca aaatttacat gaattttag     1800 aatagtctcg tatttatgcc caataatcag gaaaattacc taatgctgga ttcttgttaa   1860 taaaacaaa ataaataaat taaataaaca aataaaaatt ataagtaaat ataaatatat    1920
aagtaatata aaaaaaaagt aaataaataa ataaataaat aaaaattttt tgcaaatata   1980
taaataaata aataaaatat aaaaataatt tagcaaataa attaaaaaaa aaaaaaaaaa   2040
a                                                                   2041
```